US012630878B2

(12) United States Patent
Taoufik et al.

(10) Patent No.: US 12,630,878 B2
(45) Date of Patent: May 19, 2026

(54) METHOD FOR STRATIFYING THE RISK OF BK VIRUS NEPHROPATHY AFTER A KIDNEY TRANSPLANT

(71) Applicants: UNIVERSITE PARIS-SACLAY, Saint Aubin (FR); INSTITUT NATIONAL DE LA SANTE ET DE LA RECHERCHE MEDICALE (INSERM), Paris (FR); ASSISTANCE PUBLIQUE—HOPITAUX DE PARIS, Paris (FR)

(72) Inventors: Yassine Taoufik, Paris (FR); Antoine Durrbach, Paris (FR); Manon Dekeyser, Paris (FR)

(73) Assignees: Universite Paris-Saclay, Saint Aubin (FR); Institut National de la Sante et de la Recherche Medicale (INSERM), Paris (FR); Assistance Publique—Hopitaux de Paris, Paris (FR)

( * ) Notice: Subject to any disclaimer, the term of this patent is extended or adjusted under 35 U.S.C. 154(b) by 1303 days.

(21) Appl. No.: 17/253,195

(22) PCT Filed: Jun. 18, 2019

(86) PCT No.: PCT/EP2019/066100
§ 371 (c)(1),
(2) Date: Dec. 17, 2020

(87) PCT Pub. No.: WO2019/243372
PCT Pub. Date: Dec. 26, 2019

(65) Prior Publication Data
US 2021/0301344 A1 Sep. 30, 2021

(30) Foreign Application Priority Data
Jun. 18, 2018 (FR) ...................................... 1855342

(51) Int. Cl.
*C12Q 1/6883* (2018.01)
*C12Q 1/686* (2018.01)
*C12Q 1/70* (2006.01)

(52) U.S. Cl.
CPC ........... *C12Q 1/6883* (2013.01); *C12Q 1/686* (2013.01); *C12Q 1/701* (2013.01); *C12Q 2600/156* (2013.01)

(58) Field of Classification Search
CPC ...... C12Q 1/6883; C12Q 1/686; C12Q 1/701; C12Q 2600/156; G01N 2333/025; G01N 2800/60
See application file for complete search history.

(56) References Cited

U.S. PATENT DOCUMENTS

| | | | | |
|---|---|---|---|---|
| 7,892,795 B2 * | 2/2011 | Chen | ...................... | C12Q 1/701 435/325 |
| 2009/0246754 A1 * | 10/2009 | Kiefer | .................... | C12Q 1/701 435/5 |
| 2011/0091866 A1 * | 4/2011 | Iwaki | ...................... | C12Q 1/701 435/5 |
| 2016/0348174 A1 * | 12/2016 | Sarwal | .................... | A61P 13/12 |
| 2018/0127838 A1 * | 5/2018 | Mehta | .............. | G01N 33/56983 |

FOREIGN PATENT DOCUMENTS

WO WO-2017060283 A1 * 4/2017 ............. A61K 39/12

OTHER PUBLICATIONS

Sawinski et al., (Nephrol Dial Transplant (2015) 30: 209-217 (Year: 2015).*
Schaenman et al., *Increased Freqeuncy of BK Virus-Specific Polyfunctional CD8+ T Cells Predict Successful Control of BK Viremia after Kidney Transplantation*, 101(6) Transplantation 1479-1487 (jun. 2017).
Smith et al., *BK Virus Nephropathy in Pediatric Renal Transplant Recipients: An Analysis of the North American Pediatric Renal Trials and Collaborative Studies (NAPRTCS) Registry*, 2 Clin. J. Am. Soc. Nephrol. 1037-1042 (2007).
Van Aalderen et al., *Clincially Relevant Reactivation of Polyomavirus BK (BKPyV) in HLA-A02-Positive Renal Transplant Recipients Is Associated with Imparied Effector-Memory Differentation of BKPyV-Specific CD8+ T Cells*, 12(10) PLoS Pathog. 1-25 (2016).
Awadalla et al., *HLA Mismatching Increases the Risk of BK Virus Nephropathy in Renal Transplant Recipients*, 4 American Journal of Transplantation 1691-1696 (2004).
Batal et al., *Measurements of Global Cell-Mediated Immunity in Renal Transplant Recipients With BK Virus Reactivation*, 129 American Society for Clinical Pathology 587-591 (2008).
Chung et al., *Clinical usefulness of BK virus plasma quantitative POR to prevent BK virus associated nephropathy*, 25 European Society for Organ Transplantation 687-695 (2012).
(Continued)

*Primary Examiner* — Fereydoun G Sajjadi
*Assistant Examiner* — Joel D Levin
(74) *Attorney, Agent, or Firm* — Panitch Schwarze Belisario & Nadel LLP; Erin M. Dunston

(57) ABSTRACT

The present application describes and claims a novel method for identifying and stratifying the risk of developing a BK virus nephropathy ("Nx BK-v" below) in patients having undergone a kidney transplant. This method uses an index combining at least three bio-markers: i) the intensity of the anti-BK-v memory T lymphocyte response (memory T lymphocytes which are specific to BK-v, hereinafter "LTm anti-BK-v"), ii) the number of occurrences of incompatibility in the HLA alleles of class I and class II between the donor and the recipient of the graft, taking into account iii) the viral charge of the BK-v virus in the whole blood of the patient. The present method allows a very precise evaluation of the risk of developing an Nx BK-v during the months following the test with the aim of optimising the immunosuppressive treatment in order to better preserve the transplanted kidney.

13 Claims, 18 Drawing Sheets

Specification includes a Sequence Listing.

(56)            References Cited

OTHER PUBLICATIONS

Comoli et al., *Immunity to Polyomavirus BK Infection: Immune Monitoring to Regulate the Balance between Risk of BKV Nephropathy and Induction of Alloimmunity*, 2013 Clinical and Developmental Immunology 1-6 (2013).

Comoli et al., *Polyomavirus-associated nephropathy: update on BK virus-specific immunity*, 8 Transplant Infectious Disease 86-94 (2006).

Couchoud et al., *Rapport annuel Rein 2015*, Agence De La Biomédecine 1-87 (2015).

Dalianis et al., *Human polyomaviruses in disease and cancer*, 437 Virology 63-72 (2013).

Dekeyser et al., *Polyomavirus-specific cellular immunity: from BK-virus-specific cellular immunity to BK-virus-associated nephropathy?* 6(307) Frontiers in Immunology 1-7 (Jun. 16, 2015).

Dekeyser, M., *Anomalies de la mémoire lymphocytaire T antivirale et infections virales en transplantation rénale*, Theses. fr., Feb. 18, 2019, XP055606774, 2 pages, Retrieved from the Internet: URL: http://www.theses.fr/2019SACLS065# [retrieved Jul. 18, 2019].

Drachenberg et al., *Negative Impact of Human Leukocyte Antigen Matching in the Outcome of Polyomavirus Nephropathy*, 80(2) Transplantation 276-278 (2005).

Eckardt et al., *Kidney Disease: Improving Global Outcomes (KDIGO) Transplant Work Group. KDIGO clinical practice guideline for the care of kidney transplant recipients*, 9(Suppl 3) American Journal of Transplantation S1-S157 (2009).

Egli et al., *State-of-the-Art Monitoring of Cytomegalovirus-Specific Cell-Mediated Immunity After Organ Transplant: A Primer for the Clinician*, 55 Clinical Infectious Diseases 1678-1689 (2012).

Godinho Pinto et al., *Screening for BK virus nephropathy in kidney transplant recipients: comparison of diagnostic tests*, 38(3) J. Bras. Nefrol. 356-362 (2016).

Hässig et al., *Association of BK viremia with human leukocyte antigen mismatches and acute rejection, but not with type of calcineurin inhibitor*, 16 Transplant Infectious Disease 44-54 (2014).

Helanterä et al., *BK virus viremia in a well-HLA-matched kidney transplant population mainly on low-dose cyclosporine-based immunosuppression*, 26 Clinical Transplantation E596-E601 (2012).

Hirsch et al., *European perspective on human polyomavirus infection, replication and disease in solid organ transplantation*, 20(Suppl. 7) Clin. Microbiol. Infect. 74-88 (Jan. 29, 2014).

Hirsch et al., *Polyomavirus BK Replication in De Novo Kidney Transplant Patients Receiving Tacrolimus or Cyclosporine: A Prospective, Randomized, Multicenter Study*, 13 American Journal of Transplantation 136-145 (2013).

Hirsch et al., *Prospective Study of Polyomavirus Type BK Replication and Nephropathy in Renal-Transplant Recipients*, 347(7) The New England Journal of Medicine 488-496 (Aug. 15, 2002).

International Search Report issued in International Application No. PCT/EP2019/066100 (Aug. 2, 2019).

Johnston et al., *Treatment of Polyomavirus Infection in Kidney Transplant Recipients: A Systematic Review*, 89(9) Transplantation 1057-1070 (May 15, 2010).

Lanot et al., *BK virus infections in kidney transplantation*, 12 Néphrologie & Thérapeutique 76-85 (2016) (First Page English Abstract).

Limaye et al., *Quantitation of BK Virus Load in Serum for the Diagnosis of BK Virus-Associated Nephropathy in Renal Transplant Recipients*, 183 The Journal of Infectious Diseases 1669-1672 (2001).

Pello et al., *BKV-specific T cells in the treatment of severe refractory haemorrhagic cystitis after HLA-haploidentical haematopoietic cell transplantation*, 98 Eur. J. Haematol. 632-634 (2017).

Ramos et al., *Clinical Course of Polyoma Virus Nephropathy in 67 Renal Transplant Patients*, 13 Journal of the American Society of Nephrology 2145-2151 (2002).

Rapport Annuel 2016, 380 pages (2016).

Restifo et al., *Lineage relationship of effector and memory T cells*, 25(5) Curr. Opin. Immunol. 1-12 (Oct. 2013).

Schachtner et al., *BK Virus-Specific Immunity Kinetics: A Predictor of Recovery From Polyomavirus BK-Associated Nephropathy*, 11 American Journal of Transplantation 2443-2452 (2011).

Schachtner et al., *The Loss of BKV-Specific Immunity From Pretransplantation to Posttransplantation Identifies Kidney Transplant Recipients at Increased Risk of BKV Replication*, 15 American Journal of Transplantation 2159-2169 (2015).

Sester et al., *The "ABC" of Virus-Specific T Cell Immunity in Solid Organ Transplantation*, 16 American Journal of Transplantation 1697-1706 (2016).

Sharma et al., *BK Virus in Kidney Transplant: Current Concepts, Recent Advances, and Future Directions*, 4 Experimental and Clinical Transplantation 377-384 (2016).

Stankoff et al., *Leucoencéphalite multifocale progressive*, Neurologie 1-9 (2010).

Suleiman et al., *HLA Mismatching and cPRA Do Not Affect BK Viremia and Nephropathy Risk in Kidney Transplantation: A Retrospective Analysis*, Meeting: 2018 American Transplant Congress 1-4 (Jun. 4, 2018) (Abstract).

Thangaraju et al., *Risk Factors for BK Polyoma Virus Treatment and Association of Treatment With Kidney Transplant Failure: Insights From a Paired Kidney Analysis*, 100(4) Transplantation 854-861 (2016).

Written Opinion issued in International Application No. PCT/EP2019/066100 (Aug. 2, 2019).

Brennan, D. C. et al. Incidence of BK with tacrolimus versus cyclosporine and impact of preemptive immunosuppression reduction. Am. J. Transplant. 5, 582-594 (2005).

Cleenders, E. et al. An observational cohort study of histological screening for BK polyomavirus nephropathy following viral replication in plasma. Kidney Int 104, 1018-1034 (2023).

Dekeyser et al., *Allogeneic CD4 T Cells Sustain Effective BK Polyomavirus-Specific CD8 T Cell Response in Kidney Transplant Recipients*, 9 Kidney International Report 2498-2513 (2024).

Dekeyser, M., François, H., Beaudreuil, S. & Durrbach, A. Polyomavirus-Specific Cellular Immunity: From BK-Virus-Specific Cellular Immunity to BK-Virus-Associated Nephropathy? Front Immunol 6, 307 (2015).

Drachenberg, C. B. et al. Negative impact of human leukocyte antigen matching in the outcome of polyomavirus nephropathy. Transplantation 80, 276-278 (2005).

Egli, A., Köhli, S., Dickenmann, M. & Hirsch, H. H. Inhibition of polyomavirus BK-specific T-Cell responses by immunosuppressive drugs. Transplantation 88, 1161-1168 (2009).

Freitas, M. C. S. Kidney transplantation in the US: an analysis of the OPTN/UNOS registry. Clin Transpl 1-16 (2011).

Ginevri, F. et al. Prospective monitoring of polyomavirus BK replication and impact of pre-emptive intervention in pediatric kidney recipients. Am. J. Transplant. 7, 2727-2735 (2007).

Hirsch, H. H., Yakhontova, K., Lu, M. & Manzetti, J. Bk Polyomavirus Replication in Renal Tubular Epithelial Cells Is Inhibited by Sirolimus, but Activated by Tacrolimus Through a Pathway Involving FKBP-12. Am J Transplant 16, 821-832 (2016).

Hirsch, HH. et al. Polyomavirus BK replication in de novo kidney transplant patients receiving tacrolimus or cyclosporine: a prospective, randomized, multicenter study. Am. J. Transplant. 13, 136-145 (2013).

Kaech, S. M. & Ahmed, R. Immunology. CD8 T cells remember with a little help. Science 300, 263-265 (2003).

Leboeuf, C. et al. BK Polyomavirus-Specific 9mer CD8 T Cell Responses Correlate With Clearance of BK Viremia in Kidney Transplant Recipients: First Report From the Swiss Transplant Cohort Study. Am. J. Transplant. (2017).

Opelz, G., Döhler, B., Middleton, D., Süsal, C., & A Collaborative Transplant Study Report. HLA Matching in Pediatric Kidney Transplantation: HLA Poorly Matched Living Donor Transplants Versus HLA Well-Matched Deceased Donor Transplants. Transplantation 101, 2789-2792 (2017).

Schachtner, T et al. BK virus-specific immunity kinetics: a predictor of recovery from polyomavirus BK-associated nephropathy. Am. J. Transplant. 11, 2443-2452 (2011).

(56)          References Cited

OTHER PUBLICATIONS

Thangaraju, S. et al. Risk Factors for BK Polyoma Virus Treatment and Association of Treatment With Kidney Transplant Failure: Insights From a Paired Kidney Analysis. Transplantation 100, 854-861 (2016).

* cited by examiner

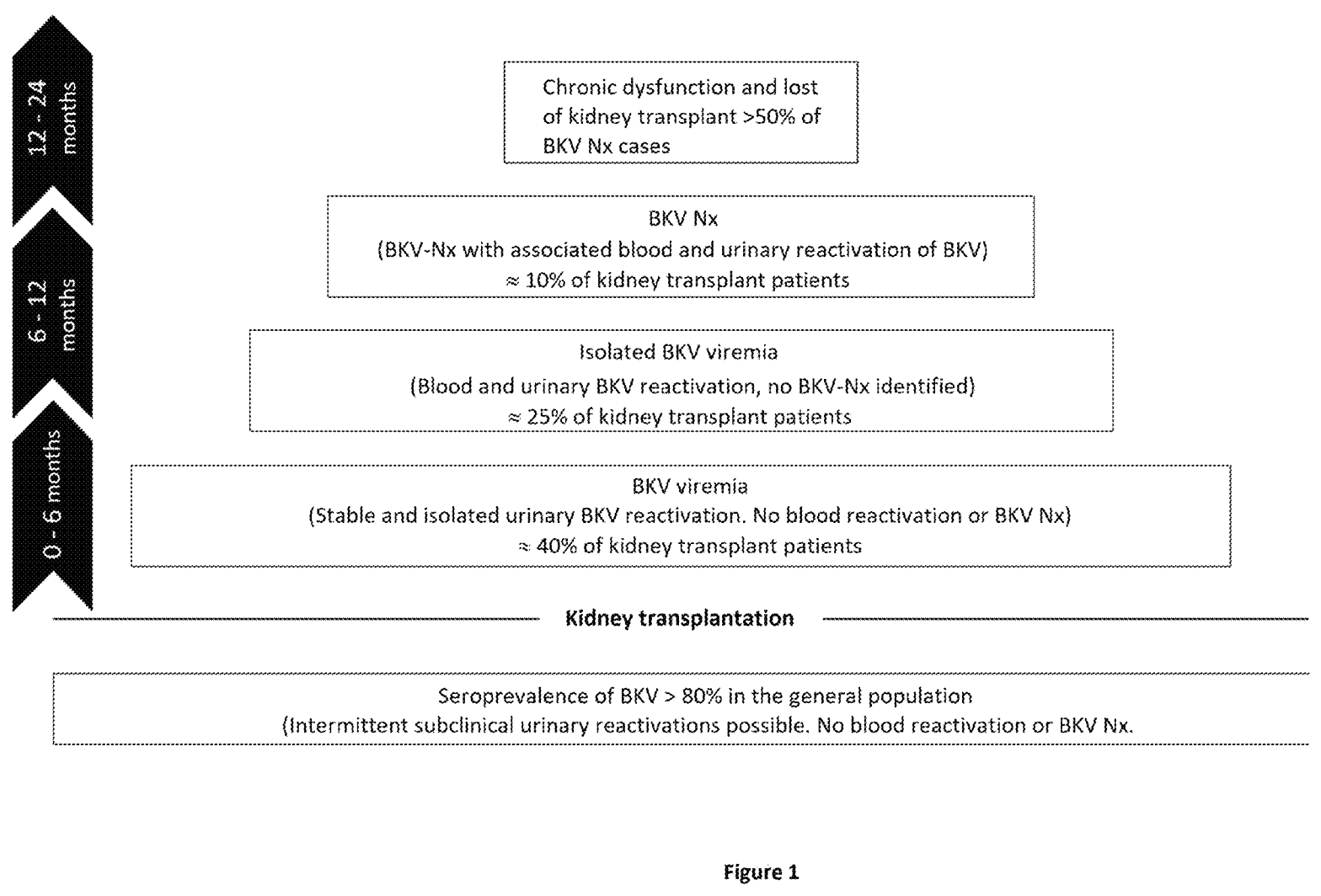

Chronic dysfunction and lost of kidney transplant >50% of BKV Nx cases

BKV Nx
(BKV-Nx with associated blood and urinary reactivation of BKV)
≈ 10% of kidney transplant patients Isolated BKV viremia
(Blood and urinary BKV reactivation, no BKV-Nx identified)
≈ 25% of kidney transplant patients BKV viremia
(Stable and isolated urinary BKV reactivation. No blood reactivation or BKV Nx)
≈ 40% of kidney transplant patients Kidney transplantation Seroprevalence of BKV > 80% in the general population
(Intermittent subclinical urinary reactivations possible. No blood reactivation or BKV Nx.

12 - 24 months

6 - 12 months

0 - 6 months

Figure 1

Figure 2
a – Assessment of renal function according to the forms
of BKV virus reactivation
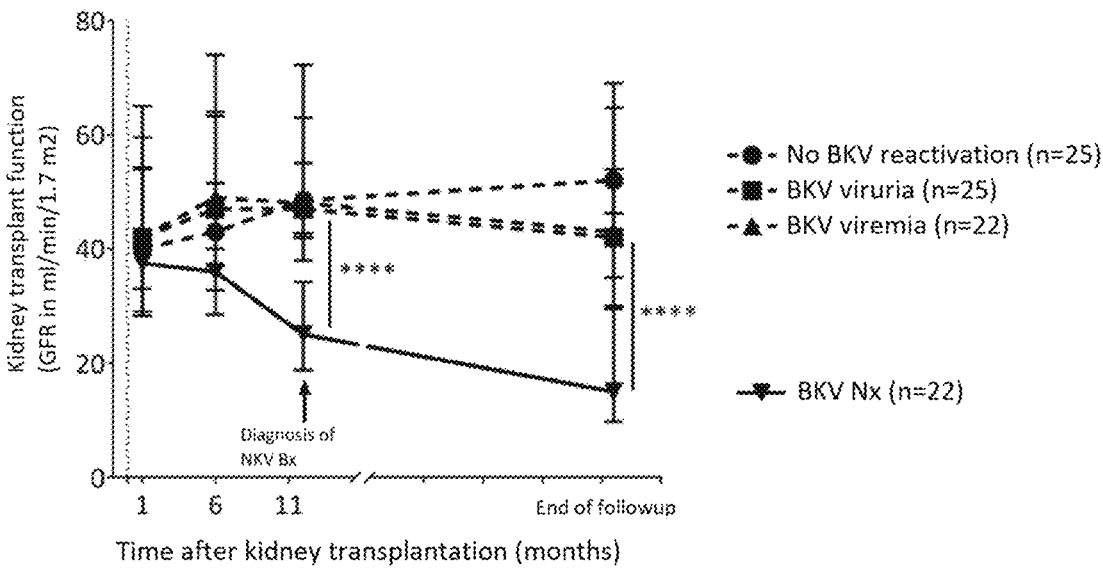
b - Kidney transplant survival according to the forms of
BKV virus reactivation
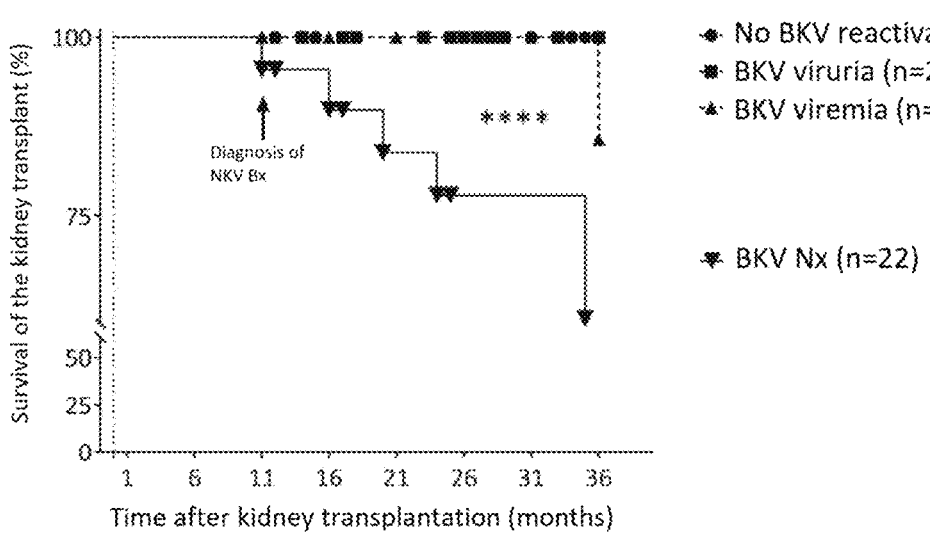

Combination of three parameters:

Figure 5
BKV virus viral load in the different patient groups of the cohort
a – Copies/mL in the blood
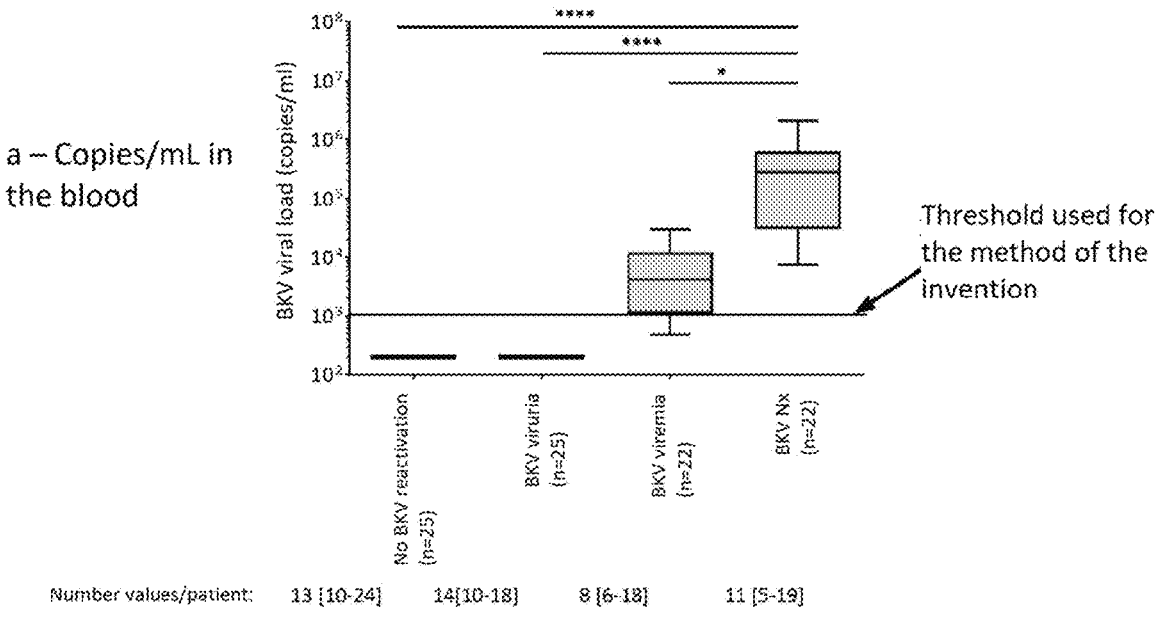
b – Copies/mL in the urine
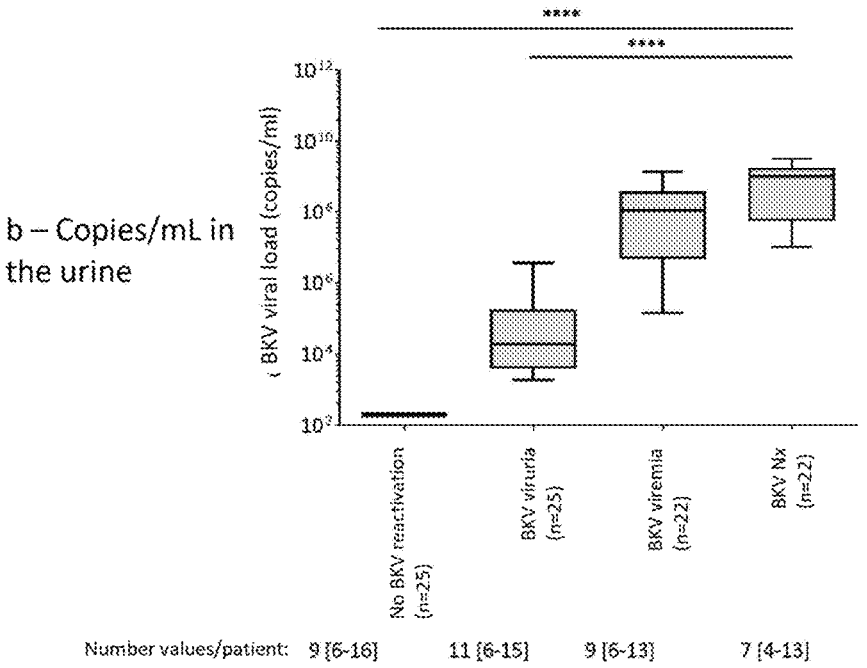

1/ Anti-BK-v memory T lcell response: specific stimulation by BKV virus peptides a – Cytokine secretions

2/ Global anti-viral memory T cell response: stimulation by a pool of anti-viral peptides covering the cytomegalovirus, Epstein-Barr and influenza viruses a – Cytokine secretions Cytokine secretions b – Proliferation Intensity of the anti-BKV TCm proliferative response as a function of BKV viral load (copies/mL of blood)

Figure 8

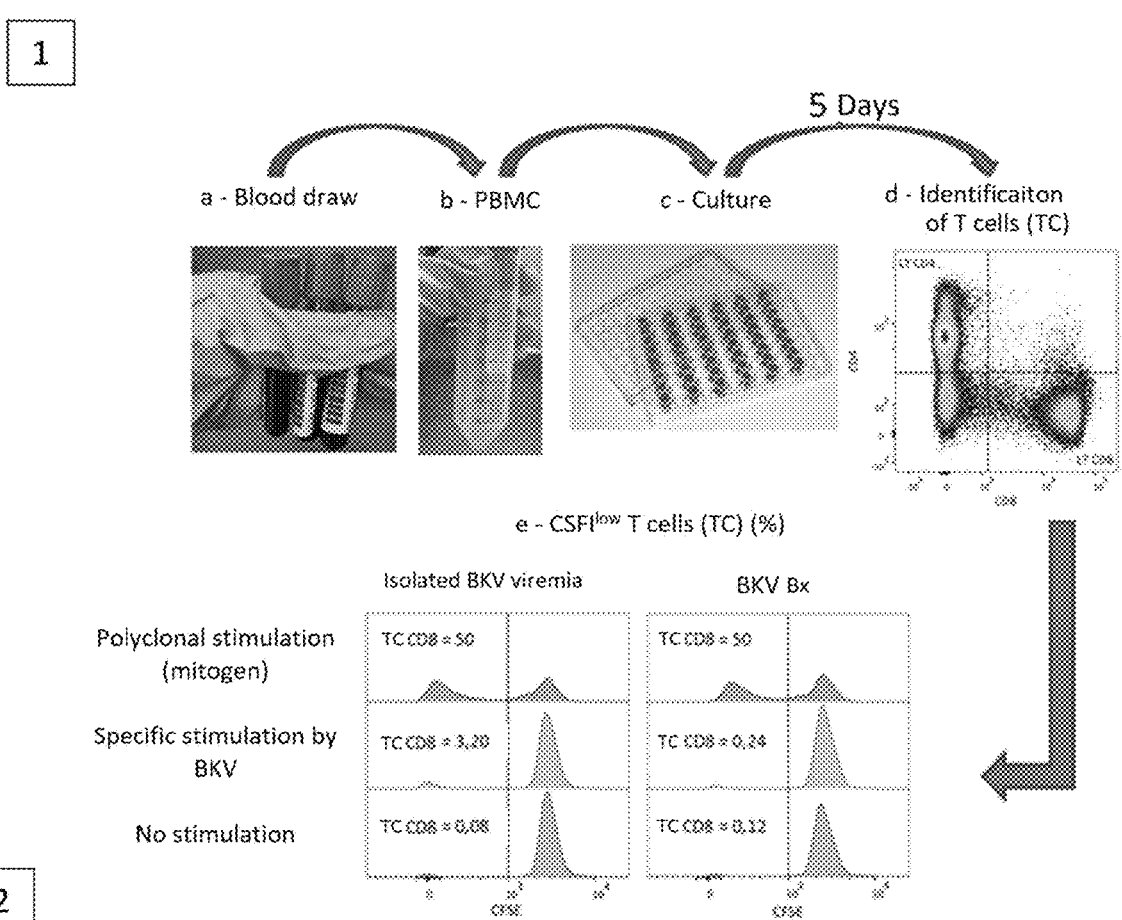

| Assessment of the normalized intensity of the anti-BKV TCm response | BKV viremia | BKV Nx 1 | BKV Nx 2 |
|---|---|---|---|
| a - Proportion of CD8 CFSE^low (%) anti-BKV TCm | 3.12 | 0.12 | 0.16 |
| b - Proportion of CD8 CFSE^low expressed per 1x10^6 total CD8 T cells (%*10^4) | 31,200 | 1,200 | 1,600 |
| c - BKV viral load (copies/ml) | 2.0x10^4 | 2.1.10^4 | 4.3x10^5 |
| d - Normalized intensity of the anti-BKV TCm response Normalized intensity measurement unit Proportion of CD8 CFSE^low (%) anti-BKV TCm (%) expressed per per 1x10^6 total CD8 T cells (%*10^4) and normalized for 1x10^3 copies of BKV per mL of blood | 1 560 | 57 | 4 |

Normalized intensity of the anti-BKV TCm response per $10^3$ copies/mL of BKV (number of CFSE$^{low}$ T cells)

| Functional BKV TC (normalized intensity measurement unit) | CD4 | CD8 |
|---|---|---|
| BKV viremia (n=11) | 810 [1.6 - 8897] | 448.9 [0.1 - 31281] |
| BKV Nx (n=16) | 2.1 [0.1 - 21.5] | 0.1 [0.1 - 5.9] |
| $p$ | 0.0016 | 0.0001 |

Figure 11
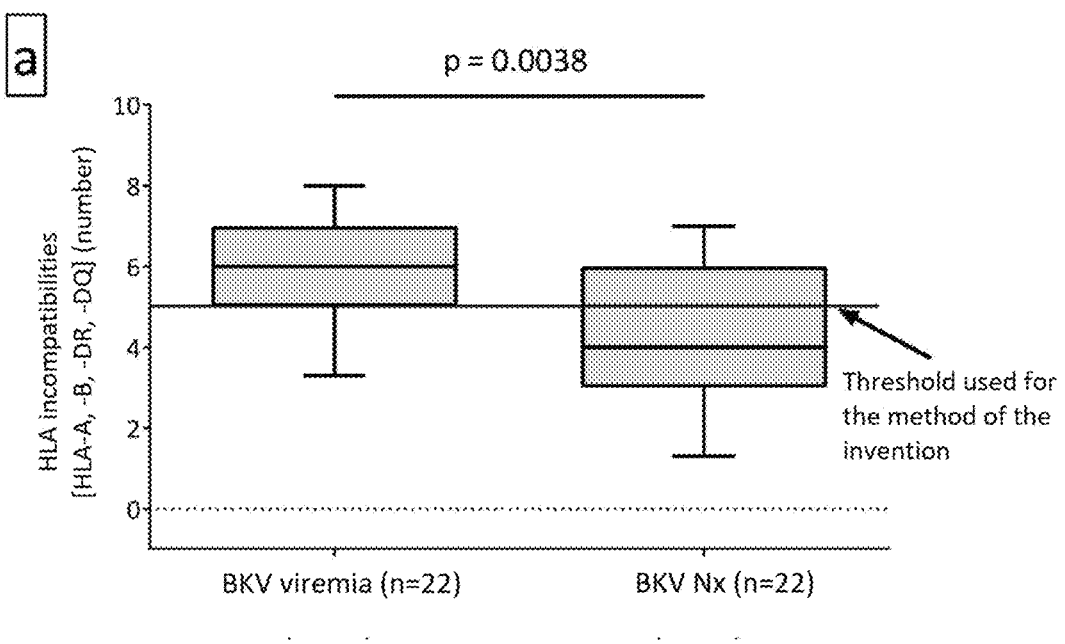
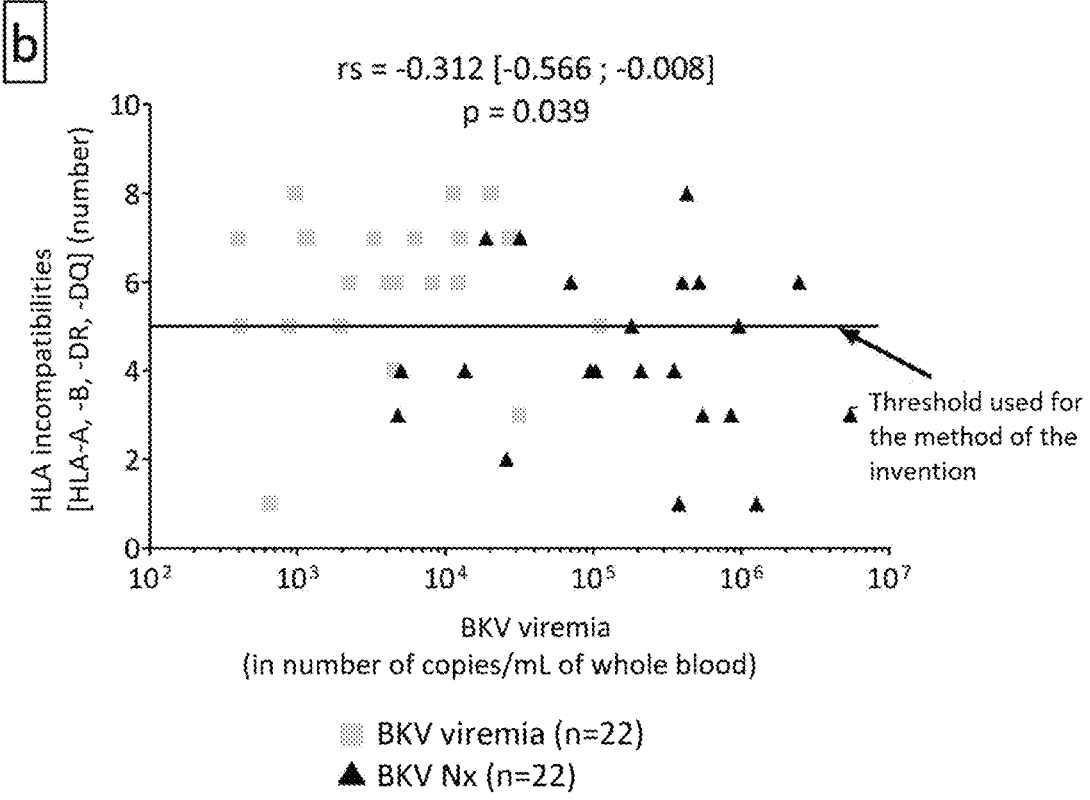

BKV Nx risk as a function of:
i. intensity of the anti-BKV TCm response
ii. normalized to the BKV viral load in the blood and
iii. number of HLA incompatibilities

Indications for the method of the invention

SEQUENCE LISTING

```
<160> NUMBER OF SEQ ID NOS: 3

<210> SEQ ID NO 1
<211> LENGTH: 20
<212> TYPE: DNA
<213> ORGANISM: ARTIFICIAL
<220> FEATURE:
<223> OTHER INFORMATION: amorce sens de 5'-3' pour amplifier BK-V

<400> SEQUENCE: 1
catagcatgc aagggcagtg                                              20

<210> SEQ ID NO 2
<211> LENGTH: 20
<212> TYPE: DNA
<213> ORGANISM: artificial
<220> FEATURE:
<223> OTHER INFORMATION: Amorce antisens de 5' en 3' pour amplifier BK-V

<400> SEQUENCE: 2
gagctgcctg gggaaatctt                                              20

<210> SEQ ID NO 3
<211> LENGTH: 20
<212> TYPE: DNA
<213> ORGANISM: artificial
<220> FEATURE:
<223> OTHER INFORMATION: sonde PCR

<400> SEQUENCE: 3
taggccattc cttgcagtac                                              20
```

METHOD FOR STRATIFYING THE RISK OF BK VIRUS NEPHROPATHY AFTER A KIDNEY TRANSPLANT

CROSS-REFERENCE TO RELATED APPLICATIONS

This application is a U.S. National Stage Application pursuant to 35 U.S.C. § 371 of International Patent Application PCT/EP2019/066100, filed on Jun. 18, 2019, and published as WO 2019/243372 on Dec. 26, 2019, which claims priority to French Patent Application 1855342, filed on Jun. 18, 2018, all of which are incorporated herein by reference in their entireties for all purposes.

SUMMARY OF THE INVENTION

The present invention describes and claims a new method to identify and stratify the risk of developing BK virus nephropathy (hereinafter "BKV Nx") in patients who had a kidney transplantation. This method uses an index combining at least three biomarkers: i) the intensity of the anti-BKV memory T cell response (memory T cells specific for BKV, hereinafter "anti-BKV TCm"), ii) the number of incompatibilities on class I and class II HLA alleles between the transplant donor and the recipient, taking into account iii) the BKV viral load in the patient's blood. The present method enables the risk of developing a BKV Nx in the month following the test to be assessed very precisely, for purposes of optimizing immunosuppressive treatment to better preserve the transplanted kidney.

DESCRIPTION OF THE PRIOR ART

The following abbreviations were used in the present application:

BKV: Human BK Polyomavirus
CFSE: Carboxyfluorescein succinimidylester, a lymphocyte proliferation marker
HLA: Human Leukocyte Antigens
JCV: Human JC Polyomavirus
anti-BKV TCm: memory T cells specific for BKV
BKV Nx: BK virus nephropathy
anti-BKV TCm response: response of memory T cells specific for BKV
End-Stage Chronic Renal Disease and its Replacement Therapies End-stage chronic renal disease is the complete and definitive impairment of kidney function requiring the use of a kidney replacement treatment (by dialysis or transplantation). In France, for 2015, the prevalence of end-stage chronic renal disease was 82,295 patients, or 1,232 per million inhabitants.

Kidney transplantation is currently the most effective treatment for end-stage chronic renal disease. Compared to maintaining dialysis, kidney transplantation improves patient survival and quality of life, with a reduced financial cost. It is the largest solid organ transplantation activity worldwide.

In 2014, the Global Observatory for Organ Donation and Transplantation (GODT, an organization of the World Health Organization) recorded 119,873 transplant patients worldwide, including 79,948 (67%) kidney transplant patients. In France, in 2015, the estimated number of patients with a functional kidney transplant was 36,729, or a prevalence of 552.4 cases per million inhabitants, thus representing 44.6% of the 82,295 patients treated for end-stage chronic renal disease.

Due to the current shortage of organs to meet all the kidney transplantation needs (1 kidney transplant available for 4.7 people awaiting one with a median wait time of 18.5 months), it is indispensable to increase the longevity of kidney transplants, currently estimated at 13 years. ([1], [2]). To this end, transplant patients are routinely subjected to immunosuppressive therapy. This measure is actually indispensable to control the allogeneic immune response and increase transplant survival. However, therapeutic immunosuppression can be associated with complications, especially infectious complications, that can be detrimental for the transplant. These infections can lead to the loss of the transplanted kidney, thus requiring the patient to return to dialysis (with all the resulting harmful consequences) and leading to an increase in the number of patients awaiting kidney transplant.

Reactivation of BK and JC Polyomavirus in Kidney Transplantation

Viral reactivations are very common complications in immunocompromised patients. Particularly, the reactivation of certain Polyomaviruses is particularly concerning. In humans, there are currently 13 known species of Polyomavirus. It is a very common virus, infecting many animal species with species specificity. The seroprevalence of these viral infections is very high globally (80-90% at adult age), indicating an early and broad viral exposure. The two main representatives are BK virus (BKV) and JC virus (JCV). The common characteristic of these viruses is their ability to persist long term asymptomatically in the body, and to become pathogens in situations of immunosuppression ([3], [4]).

After transplantation, BKV is known to infect epithelial cells of the urinary tract and the renal parenchyma of the transplanted kidney. In kidney transplant patients, reactivation of BK virus can lead to a detectable viral load in the blood (>200 copies/mL).

Thus, in the context of kidney transplantation, BKV is responsible for nephropathies (hereinafter BKV Nx), kidney failure or ureteral strictures ([4]). In the context of hematopoietic stem cell transplants, BKV is responsible for hemorrhagic cystitis ([4]).

Several levels of BKV reactivations are observed in patients who had a kidney transplantation (FIG. 1).

The patients may present:

—1—"BKV viruria" with no detectable viremia or renal involvement. In these patients, BKV is replicating in the urinary tract. Viruira is observed in nearly 40% of kidney transplant patients and conventionally occurs in the first 3 to 6 months post transplant.

—2—"Isolated BKV viremia" with no specific kidney damage detectable in the kidney transplant. Such viremia is observed in nearly 24% of kidney transplant patients and conventionally occurs in the first 12 months post kidney transplantation.

—3—BKV Nx. In these patients, in addition to viremia and viruria, viral replication in the kidney transplant is observed, responsible for specific kidney damage. Diagnosis is currently histological and shows nuclear viral inclusions (SV40 T positive antigens), nuclear dystrophies, polymorphic cell infiltration and renal fibrosis. This serious complication is diagnosed in nearly 10% of kidney transplant patients and conventionally occurs in the first 24 months post kidney transplantation. ([5]-[6]). The progression of BKV Nx depends on the extent of the renal parenchyma damage, itself related to the intensity of the viral load (see Table 8, Hirsch et al., 2014 [7]). The outcome is favorable in patients whose immune system succeeds in controlling the intraparenchymal replication of BKV. In return, the persistence of intense and prolonged intraparenchymal viral replication of BKV causes irreversible damage to the renal parenchyma, leading to chronic dysfunction, kidney disease and ultimately a loss of the transplant in more than 50% of cases.

Table 8 from Hirsch et al, Clinical Microbiology and Infection 2014 [7] shows the different histological stages of BKV Nx, as well as the renal prognosis associated with the histological damage.

FIG. 2 shows the kidney function assessment (by measurement of glomerular filtration rate—part a) and the survival rate of kidney transplants (part b) at 3 years post-transplant in patients with or without BKV Nx. These data arise from the cohort study that led to the development of this invention. This observational (noninterventional) study was conducted by the present inventors from November 2014 to November 2017 in a cohort of 94 kidney transplant patients divided into 4 groups according to their degree of BKV reactivation: one group with no BKV reactivation (n=25), one group with isolated BKV viruria (n=25), one group with isolated BKV viremia with no histologically-proven BKV Nx (n=22) and one group with histologically-proven BKV Nx (n=22). FIG. 2 shows that patients with BKV Nx have severe dysfunction of the kidney transplant. This dysfunction is present as soon as BKV Nx is diagnosed and worsens progressively, with a loss of the transplant in 50% of cases after 3 years of followup.

It is therefore essential to detect BKV Nx early in kidney transplant patients, or even anticipate it, the better to try and stop it.

Risk Factors and Current Diagnostic and Therapeutic Approaches for BKV Nx

It is known that the replication of BKV is promoted by different factors, including the nature and the intensity of immunosuppressive treatment and the impairment of the immune response specific for BKV ([8]). More precisely, the risk of developing BKV Nx is significantly associated with the intensity of immunosuppressive treatment, the combination of tacrolimus-mycophenolate mofetil (current standard treatment in kidney transplant) as well as a substantial cumulative exposure to corticosteroids (>3000 mg of corticosteroids in the 6 months preceding BKV viremia). Other risk factors unrelated to immunosuppressive treatments have also been identified, such as donor and recipient age, recipient sex or characteristics specific to the transplant such as ischemia-reperfusion damage ([7]).

Currently, there is no specific antiviral therapy for this virus. Treatments such as cidofovir are responsible for significant toxicity for kidney transplants and are contraindicated in the event of severe graft dysfunction. Furthermore, leflunomide or fluoroquinolones have proven effective in isolated cases. However, the inconsistent efficacy and insufficient number of these rare cases do not allow currently recommending the use of these drug molecules in common practice [24]).

The only currently recognized treatment for BKV Nx is reducing the therapeutic immunosuppression to which the transplant recipient is subjected ([7], [24]). Indeed, reactivation of BKV virus occurs when the activity of the immune system is reduced by immunosuppressive treatment. When BKV Nx is detected, the first therapeutic reflex is to reduce immunosuppression. However, this therapeutic adjustment is done empirically, with no quantitative limit, thus exposing the patient to a risk of allogeneic rejection and loss of the transplant. It is therefore important to resort to this therapeutic approach only in cases where the patient actually has BKV Nx or is considered to be at very high risk of developing it, and it must be done in a gradual and controlled manner. The immunosuppressive treatment must then be increased again so as not to increase the risk of transplant rejection. It is also important not to reduce immunosuppression in patients who simply have isolated BKV viremia or viruria, because this reduction endangers the transplant, even though it is not infected by BKV.

A BKV infection can be easily detected by quantitative PCR on a urine or blood sample. However, as explained above, the detection of BKV in the blood or urine of transplant patients is not necessarily associated with a poor prognosis for the transplant, since a large number of patients with viremia or viruria do not develop BKV Nx (viral reactivation is not always reached in the transplant itself). Indeed, while a BKV viral load≥$10^4$ copies/mL of blood is associated with a sensitivity of 90%, this test is not sufficiently effective for diagnosing BKV Nx since its positive predictive value does not surpass 55% ([1], [25], [26]).

Currently, immunosuppressive treatment is reduced in cases of proven or suspected BKV (BKV positive PCR for at least 4 weeks and ≥$10^4$ copies/mL of blood). However, this solution is not optimal since patients with simple isolated viremia, without involving the renal transplant, would be considered "at risk". FIG. 3 illustrates this issue.

Histological analysis of the renal parenchyma after kidney transplant biopsy is currently the only reliable method to diagnose BKV Nx. However, it is an invasive procedure with a risk of bleeding complications and can also give a false negative in 10 to 30% of cases, in particular in the early stages of BKV Nx. Moreover, in the absence of deterioration of kidney transplant function, it is not recommended to subject these patients to repeated biopsies to detect or confirm the presence of damage caused by BKV ([7]). Therefore, the currently recommended diagnostic approach for BKV Nx relies on longitudinal monitoring of BKV viral load in the patient's blood, and performing a kidney transplant biopsy in the event of deterioration of transplant function and/or a BKV viral load≥$10^4$ copies/mL of blood for at least 4 consecutive weeks. However, impaired transplant function assessed by glomerular filtration rate is a late marker in the case of BKV Nx diagnosis, associated with an already significant extension of fibrosing lesions. This irreversible damage is associated with a major risk of transplant loss (see Table 8 of Hirsch et al, 2014 [7] and FIG. 2).

Thus, the current strategy causes diagnostic delays and difficulties, while the therapeutic management of this complication must be as early as possible in order to avoid the occurrence of irreversible damage.

Other diagnostic tests for BKV Nx have been proposed in the past. These include immunovirological monitoring, which is based on the study of the functional capacities of total or antiviral T cells and aims to identify patients at the most risk of viral complications ([12]). Some authors have studied the specific anti-BKV immune response to identify patients at risk of BKV Nx ([8], [9], [27]). A low specific anti-BKV immune response, assessed by the interferon-γ secretion capacities of T cells stimulated by BKV antigens (ELISA or ELISPOT tests), has been found in patients with BKV blood reactivation ([22], [23]). Others used tests of overall lymphocyte immune response such as the "Cylex ImmunKnow Test", in the context of blood and urinary BKV reactions ([20]). In this study, the authors [20] did not demonstrate an association between the overall lymphocyte response and BKV Nx, but only with viremia. However, these methods never allowed either diagnosing BKV Nx or reliably identifying patients at risk of developing BKV Nx. The search for the best parameters is ongoing ([21]). Currently, only histology performed on a kidney biopsy allows objectively diagnosing BKV Nx ([7], [9]).

Thus, there is an urgent need to diagnose patients with BKV Nx reliably, early and non-invasively, as well as to stratify the risk of developing this complication in patients who had a kidney transplantation. These diagnostic and prognostic methods should ideally discriminate patients at risk of developing BKV Nx from those with isolated BKV viremia, with no involvement of the transplant or subsequent risk of complications of this type.

DESCRIPTION OF THE INVENTION

The present invention meets this need, by providing a noninvasive and early personalized assessment of the risk of BKV Nx. The originality of the method of the invention is based on the consideration of a combination of three parameters specific to the patient, namely i) a virological parameter assessed by the BKV viral load in the patient's blood, ii) a immunological parameter assessed by the intensity of the anti-BKV memory T cell response (anti-BKV TCm response) in the patient, and iii) the number of HLA incompatibilities in the [donor/recipient] pair (FIG. 4). These parameters must be combined to obtain a complete, reliable and reproducible index that permits individualized monitoring, at a given time t, of kidney transplant patients. This method is more reliable than tests of the prior art, since patients with isolated BKV viremia will not be classified "at risk" (out of 27 patients tested, its positive predictive value is 100% and the false positive rate is zero; see the examples below). Moreover, the use of the marker linked to anti-BKV memory T cells (anti-BKV TCm) permits early assessment of the BKV Nx risk, before the onset of irreversible damage to the renal parenchyma. Above all, this method is not very invasive (simple blood samples are required), and can therefore be reproduced at different times after the transplant, with no risk for the patient. Due to this potential repeatability, the method of the invention allows better assessing the response to therapeutic management and, ultimately, helping to modulate therapeutic immunosuppression or any other treatment that would allow controlling BKV reactivation, all without the need for kidney transplant biopsy.

DETAILED DESCRIPTION OF THE INVENTION

The method of the invention is based on the consideration of three factors, a virological parameter, an immunological parameter and a genetic parameter, which must be combined together. This allows obtaining a complete, reliable and early index for the risk of developing BKV Nx for a given patient. These factors are:
- i) the viral load of BKV virus in the patient's blood at a given time,
- ii) the intensity of the anti-BKV TCm response of the same patient at the same time,
- iii) the number of HLA molecule incompatibilities between the transplant donor and the patient/recipient, determined at the time of kidney transplant.

FIG. 4 shows the method of the invention based on the combination of these three parameters.

The combination of these markers allows individually assessing, at a given time t, the risk of occurrence of BKV Nx for the patient tested. This method thus allows individualized monitoring of renal transplant patients.

The present method has the following advantages relative to the tests proposed in the prior art:
- ➢ It integrates the BKV viral load, the intensity of the anti-BKV TCm response and the HLA allele differences in a donor/recipient pair in a multiparametric way and thus allows a more complete assessment of the immune and virological situation of each patient.
- ➢ It is fast, inexpensive, standardizable and reliable, allowing prospective monitoring of the patient, repeatable at regular time intervals depending on the patient's condition, the treatment administered and the results previously obtained.
- ➢ It is noninvasive since it only requires a 15-mL blood sample from the patient.
- ➢ It allows detecting patients at risk of BKV Nx earlier than the methods of the prior art, especially those based on cytokine secretion of T cells specific for BKV.
- ➢ Its result is an absolute, normalized value that can be compared between patients and over the life of the same patient.

In a first aspect, the present invention therefore concerns a method to assess the risk of developing a BKV Nx for a patient who had kidney transplantation, said method comprising the following steps:
- a) measuring the viral load of BKV in a biological sample from said patient,
- b) measuring the normalized intensity of the anti-BKV TCm response (for example, on the basis of specific proliferation of CD4$^+$ and/or CD8$^+$ memory T cells relative to BKV peptides) in a biological sample from said patient,
- c) determining the number of incompatibilities between the class I and II HLA of the kidney donor and said patient.

This method permits both collecting and combining parameters a), b) and c) mentioned above, to help diagnose BKV Nx or to stratify the risk of developing BKV Nx. These steps could be conducted in any order whatever. This being said, step c) has been done prior to steps a) and b) since the number of HLA incompatibilities is known at the time of the kidney transplantation.

The biological sample used in step a) is, for example, a whole blood or plasma sample while the biological sample used in step b) is preferably a whole blood sample. In an embodiment where steps a) and b) are conducted by two independent laboratories, two separate samples may be used for the measurements of steps a) and b), for example two blood samples drawn independently from one another. In the case where two separate samples are used, they were preferably sampled close together in time, typically on the same day, for example a few hours apart (between 1 and 4 hours), or even within the same hour.

In a preferred embodiment, steps a) and b) are performed by the same laboratory, with the same biological sample used for the measurements of steps a) and b). In an even more preferred embodiment, this sample is a blood sample, drawn noninvasively and painlessly, by conventional intravenous blood draw. This blood sample can be analyzed directly or processed as proposed below in regard to the measurements to be performed. The quantification of BKV viremia (expressed in number of copies/mL of blood) can be done by quantitative PCR from whole blood or plasma obtained by centrifugation from the patient's blood. Peripheral blood mononuclear cells, including anti-BKV TCm, can be isolated by Ficoll gradient from the patient's blood sample.

In the context of the present invention, the "patient" is a human or animal individual who had a kidney transplantation in their lifetime. In a preferred embodiment, said transplantation took place within the past 5 years preceding the sample taking. In an even more preferred embodiment, said transplantation took place within the past 3 years preceding the sample taking. In a most preferred embodiment, said transplantation took place within the past 24 months preceding the sample taking.

In a preferred embodiment, the method of the invention is used to make a diagnosis or prognosis for BKV Nx in a patient with BKV blood reactivation. Preferentially, the method of the invention is applied to patients whose BKV viral load is greater than 200 copies/mL in the blood.

By initially only considering kidney transplants with BKV viremia, this represents nearly 840 patients per year in France (for nearly 3500 new kidney transplantations annually) and 7200 patients per year in Europe and in the USA (for 30,000 new kidney transplantations annually).

The method of the invention can also be applied to patients treated for transplant rejection and/or risk of eventually developing BKV Nx (between 15 and 20% of all renal transplant patients, or between 5500 patients in France and 12,000 in Europe and the USA), as well as those having BKV viremia and/or unexplained deterioration of kidney function beyond the first year of transplantation.

Thus, nearly 6340 kidney transplant patients in France and more than 19,200 in Europe and the United States could be concerned by this method each year. The present method could also be reproduced periodically for monitoring the same patient.

The three steps of the method of the invention are detailed below.

a) Step a: Measurement of the BKV Viral Load in the Patient's Blood

This step consists of measuring the number of BKV copies per mL of blood from a patient's whole blood or plasma sample. This number of BKV copies can be quantified according to the standard methods described in the art. Typically, this measurement can be obtained by using PCR techniques, such as quantitative PCR.

Assessment of the BKV Viral Load

The BKV viral load per mL of patient blood and/or urine is measured routinely for all kidney transplant patients according to international recommendations. Nevertheless, it is important to remember that an isolated measurement of BKV viral load in the patient's blood and/or urine would not, alone, be the diagnostic marker for BKV Nx, since many patients with BKV viremia or viruria do not have BKV Nx (FIG. 1, [9]) Thus, this measurement is not intended to be used, as such, as a diagnostic marker for BKV Nx, as some teams have been able to propose ([10]). This last study ([10]), conducted in a small number of patients, has not been confirmed in a larger population. Moreover, the blood BKV viral load did not allow reliably distinguishing patients with BKV Nx from those with isolated BKV. Indeed, a recent meta-analysis showed that a BKV viral load$\geq 10^4$ copies/mL of blood was associated with a positive predictive value of 55% for the diagnosis of BKV Nx ([26]). FIG. 5 illustrates this concept by showing the different levels of blood and urine BKV viral loads demonstrated by the inventors to develop the present method. Moreover, in agreement with the prior art, it is important to note that while a blood BKV viral load>$10^5$ could be associated with BKV Nx with a sensitivity of nearly 100% ([26]), this parameter is late because it is already associated with renal parenchymal damage and severe chronic dysfunction of the transplant at the time of BKV Nx diagnosis (FIG. 2a). Furthermore, the fact of the absence of significant difference between patients with isolated BKV viremia and BKV Nx, the urinary BKV viral load was not taken into account in the development of the invention (FIG. 5b).

In one preferred embodiment, the biological sample used for step a) is a whole blood sample (including plasma and the formed elements of the blood, i.e., red blood cells, leukocytes and platelets) or a plasma sample.

This whole blood or plasma sample could be treated according to standard prior art techniques.

In a still more preferred embodiment, the BKV viral load is measured in step a) by quantitative PCR from a biological sample (for example, whole blood or plasma) from said patient.

Normalization of the BKV Blood Viral Load

In the context of the invention, measuring the blood BKV viral load only permits quantifying the virus in the patient's bloodstream at the time the test of the invention is performed. This viral load value measured in step a) permits normalizing the intensity of the anti-BKV TCm response obtained in step b) in order to obtain an independent index comparable between individuals. The inventors do not use it as a prognostic marker as proposed in the prior art, by comparing the viral load to a threshold (for example 4 $\log_{10}$ copies of DNA/mL for at least 4 weeks) ([9]).

More precisely, this step reveals whether viral infection is absent, present or abnormally elevated in the patient's blood, so as to weight the results obtained in step b) concerning the intensity of the anti-BKV TCm response in said patient at the time of sampling.

In a preferred embodiment of the invention, it is possible to normalize parameter b) of the method of the invention for a fixed value of BKV copies per mL of blood. From the results that allowed developing the present method, the fixed normalization value of $10^3$ copies of BKV per mL of blood was integrated as virological parameter in the calculation of the method of the invention. This normalization value of $10^3$ copies of BKV was defined in order to permit assessing the risk of BKV Nx as early as possible, as soon as the stage of isolated BKV viremia (FIG. 5a) The highest thresholds for BKV copies were late, associated with diagnoses of BKV Nx (FIG. 5a) and with renal parenchymal damage (FIG. 2a).

Nevertheless, this threshold was only a normalization threshold set by the inventors, other values can be used to normalize parameter b), as a function of the patient, patient group, etc.

The threshold positivity value for the BKV viral load is set at 200 copies/mL of blood and 3.7 $\log_{10}$, 4 $\log_{10}$ or 4.2 $\log_{10}$, for example, can be used as the normalization threshold (thresholds previously proposed in the literature ([26]).

Once normalized the result obtained in the measurement of step b) could thus be compared between individuals, or, at different time periods for the same individual. This inter-individual comparison would allow classifying the patient according to the risk level of their group, while the intra-individual comparison would allow monitoring the progression over time of the level of risk of developing BKV Nx in the same patient.

b) Step b: Evaluation of the Normalized Intensity of the Anti-BKV Memory T Cell Response This step consists of assessing, from a peripheral blood sample, the anti-BKV TCm response at a given time t by measuring the lymphocyte proliferation capacity in response to a stimulation by specific BKV peptides. The normalization of this specific immune response relative to the BKV viral load in the blood allows obtaining the normalized intensity of the anti-BKV TCm response, thus permitting intra- and inter-individual comparisons.

Assessment of the Anti-BKV TCm Response

Anti-BKV memory T cells (anti-BKV TCm) are T cells with immunoreceptors (TCR) specific for BKV antigens that have been previously activated by a prior contact with BKV. These lymphocytes retain the "memory" of their encounter with this virus during the primary viral infection. This memory allows them to better react during a new contact with this virus, by developing a fast and effective secondary response. It is important to note that the seroprevalence of human polyomaviruses is very high worldwide (80-90% at adult age for BKV and JCV), witnessing early and widespread exposure to these viruses.

The performance of this secondary response is not simply due to a quantitative increase in anti-BKV TCm. To the higher frequency of specific clones immediately recruitable at the time of a new antigenic contact is added a better functionality of these "memory" cells when they are compared to naïve cells, in terms of proliferative, cytokine secretion and cytotoxicity capacities. These increased performances of memory T cells are related to epigenetic changes in the promotors for the genes involved in the immune response.

Step b) of the method of the invention therefore consists of assessing the intensity of the anti-BKV TCm response present in the biological sample of the patient tested by measuring the proliferation capacity of anti-BKV TCm in response to stimulation by specific BKV peptides and by normalizing this response to a fixed BKV viral load (normalized intensity).

Proliferative capacity is a pivotal element in the polyfunctionality of CD4 and CD8 memory T cell responses and one of the first functionalities lost during immune dysfunctions in chronic viral infections. The proliferative capacity reflects the abundance of CD8 memory T cells in $T_{CM}$ and $T_{SCM}$ (central memory T cells and memory stem cells). These cells have high capacities for proliferation, self-renewal and differentiation into effector cells. Moreover, they provide help signals indispensable to optimal functionality of the effector cells.

It is not a question, as proposed in the prior art, of measuring the cytokine secretion of the T cells contained in the blood of patients, in the presence of BKV peptides ([9]). More precisely, it is also not a question of measuring the secretion of interferon gamma in response to a BKV antigen peptide stimulation by ELISA or ELISPOT techniques, as proposed in [22], and still less before and after transplant, as proposed in [23]. These techniques of the prior art do not allow a precise assessment of the capacities for reconstituting immunological memory. In fact, the secretion capacity of interferon-γ makes it possible to preferentially study so-called "terminal" memory cell subpopulations of the memory effector or terminal effector type. These highly differentiated lymphocyte subpopulations have few, if any, capacities for self-renewal, proliferation or lymphocyte differentiation and therefore do not make it possible to optimally assess the reconstitution capacities of antiviral immunological memory ([13], [14]). Based on the results that allowed developing the present method, the inventors were able to demonstrate that assessment of interferon-γ cytokine secretion alone is not the most relevant parameter for lymphocyte functionality to reliably and reproducibly discriminate patients with BKV viremia from patients with BKV Nx (FIG. 6/1a).

Lymphocyte proliferation is the most discriminating assessment method (FIG. 6/1b). In fact, the proliferative response was significantly weaker in patients with BKV Nx relative to the three other patient groups (without BKV reactivation, BKV viruria and isolated BKV viremia (FIGS. 6/1b)). This was not the case by assessing interferon-γ secretion, where the cytokine response was significantly weaker between patients with BKV Nx and BKV viruria, but not between patients with BKV Nx and BKV viremia (FIG. 6/1a). Moreover, the intensity of the anti-BKV TCm proliferative response (assessed by the number of CFSE$^{low}$ T cells (see below) was negatively correlated with the BKV viral load in the blood (FIG. 7).

The present inventors have therefore favored the assessment of lymphocyte proliferation over other techniques previously employed to assess the capacities for reconstituting the specific immunological memory for BKV and to develop the method of the invention.

Identification of the Anti-BKV TCm Response

In a preferred embodiment, the biological sample used in step b) is a whole blood sample. Still more preferably, the biological sample is a whole blood sample drawn from the patient painlessly by peripheral intravenous puncture.

As explained above, memory T cells are naturally present in this type of biological sample if the patient has been infected by BKV virus. These memory cells will react quickly when they are contacted (again) with BKV virus antigens.

In one particular embodiment, the mononuclear cells present in the biological sample are isolated according to standard cell purification methods. They are separated from the other components of the sample by their density, by using Ficoll-Hypaque gradients (or equivalent). After centrifugation, low density cells (lymphocytes, monocytes/macrophages, dendritic cells and other antigen-presenting cells) are suspended above the Ficoll while all other components of the sample form a pellet. The mononuclear cells can then be collected with a pipette.

In a more particular embodiment, the whole blood mononuclear cells are then stimulated with a mixture of BKV virus antigens (for example PepTivator® BKV VP1 or PepTivator® BKV LT marketed by Miltenyi Biotec®, or equivalent, at the final concentration of 1 μg/mL/peptide). Preferably, overlapping BKV peptide mixtures are used in order to overcome the HLA differences between patients. The anti-BKV TCm present in the sample will thus proliferate actively in contact with these antigens. This stimulation can last several days (typically 4 to 7 days, preferably 5 days).

Thus, the anti-BKV CD4$^+$ or CD8$^+$ TCm response measured in step b) of the method of the invention is preferably determined by contacting mononuclear cells from the peripheral blood of said patient with BKV virus peptides, and by evaluating the proliferation of T cells present in said mononuclear cells after a few days of culture (typically 4 to 7 days, preferably 5 days of culture). This proliferation can be measured by detecting the expression of a cellular division marker (CFSE or equivalent) whose intensity decreases during cell division, each daughter cell containing half the marker contained in the mother cell. In order to specifically identify anti-BK TCm that actively proliferated, this lymphocyte proliferation is subtracted from the spontaneous T cell proliferation of said patient (since T cells were cultured under the same conditions, for the same amount of time without BKV peptides).

Even more preferably, said specific proliferation of anti-BKV TCm is measured by determining the proportion of CD4$^+$ or CD8$^+$ T cells having diluted the CFSE (or an equivalent cell division marker), present after a few days of culture in the presence of said peptides (typically 4 to 7 days, preferably 5 days of culture), and by subtracting from it the proportion of CD4$^+$ or CD8$^+$ T cells having diluted the CFSE (or an equivalent cell division marker), during the same time, but in the absence of said peptides.

Even more preferably, said specific proliferation of anti-BKV CD4$^+$ TCm is measured by comparing the proportion of CD4$^+$ T cells having diluted the CFSE (or an equivalent cell division marker) in the culture in the presence of the peptides, with the proportion of said lymphocytes having diluted the same marker and cultured under the same culture conditions, but without said peptides.

Even more preferably, said specific proliferation of anti-BKV CD8$^+$ TCm is measured by comparing the proportion of CD8$^+$ T cells having diluted the CFSE (or an equivalent cell division marker) in the culture in the presence of the peptides, with the proportion of said lymphocytes having diluted the same marker and cultured under the same culture conditions, but without said peptides.

The intensity of the anti-BKV TCm response can be measured by using any standard proliferation marker (CFSE, $^3$TH, BRDU or equivalent, etc).

CD4$^+$ and CD8$^+$ positive T cells can then be identified by flow cytometry using commercial anti-CD4 and anti-CD8 antibodies.

In a preferred embodiment, step b) uses peripheral blood mononuclear cells purified by any conventional method known in the art (for example using cell separation medium from PAN BIOTECH, ref. P04-60505).

CD4$^+$ and/or CD8$^+$ T cells having proliferated following specific BKV antigenic stimulation can be referred to as "responder" or "functional" memory cells, since they respond to specific antigenic stimulation and exhibit the typical proliferation kinetics of memory cells.

After a few days of culture (typically 4 to 7 days, preferably 5 days of culture) in the presence of specific BKV peptides, the proliferation test provides information on the number of CD4$^+$ or CD8$^+$ anti-BKV memory T cells initially present in the patient's sample.

After specific peptide stimulation, the proportion of TC that diluted the CFSE (CFSE$^{low}$ TC) is linked to the presence of functional anti-BKV TCm initially present in the sample. The proportion of CFSE$^{low}$ TC measured in the presence of peptide stimulation is corrected by substraction of the proportion of CFSE$^{low}$ TC obtained in the absence of BKV peptides.

FIG. 8/1 illustrates the identification protocol for the anti-BKV TCm response, via analysis of the proliferation of anti-BKV TCm in response to a pool of specific BKV peptides (proportion of CFSE$^{low}$ TC).

Assessment of the Normalized Intensity of the Anti-BKV TCm Response

From the proportion of CFSE$^{low}$ anti-BKV TCm obtained above, the intensity of the anti-BKV TCm response can be quantified into "normalized intensity measurement unit".

A "normalized intensity measurement unit" is defined here as being the proportion of CFSE$^{low}$, anti-BKV TCm expressed for 10$^6$ total T cells and normalized for 10$^3$ copies of BKV per mL of blood.

In practice, this "normalized intensity measurement unit" is obtained by multiplying the proportion of anti-BKV TCm obtained above by 10,000, then by normalizing the figure thus obtained for 10$^3$ copies of BKV per mL of blood (taking into account the actual viral load of the patient being tested, as measured in step a).

More explicitly, this proportion of CFSE$^{low}$ anti-BKV TCm (expressed for 10$^6$ total T cells) is normalized to a fixed number of BKV copies per mL of blood and thus reflects the normalized intensity of the anti-BKV TCm response for a given viral load. This normalization of the intensity of the anti-BKV TCm response permits an intra- and inter-individual comparison.

FIG. 8/2 is an example of the assessment of the normalized intensity of the anti-BKV TCm response.

For example:

if the proportion of CFSE$^{low}$ anti-BKV TCm, measured by lymphocyte proliferation, is 3.12% (proportion of CFSE$^{low}$ TC=3.20% after stimulation by BKV peptides (0.08% without said peptides) FIGS. 8/1e and 8/2a: "BKV viremia" example).

Thus, this proportion of CFSE$^{low}$ T-lymphocytes expressed for 10$^6$ total T cells is 31,200 (3.12*10,000) (FIG. 8/2b— "BKV viremia" example)

and if the patients viral load tested is 2×10$^4$ copies of BKV per mL of blood (FIG. 8/2c—"BKV viremia" example), then the normalized intensity measurement unit of the anti-BKV TCm response is:

[31,200*1×10$^3$]/2.0×10$^4$=1560 (FIG. 8/2d—"BKV viremia" example).

This normalized intensity measurement unit of the anti-BKV TCm response specific to each individual is compared to a threshold value. From the results that allowed developing the present method, the threshold value of 10$^2$ was integrated as immunological parameter in the calculation of the method of the present invention. This threshold value of 10$^2$ was defined as a function of the extent of the distribution of the normalized intensity of the anti-BKV TCm response in the group of patients with BKV Nx (FIG. 9).

More explicitly, patients with BKV Nx present a lower normalized intensity of anti-BKV TCm response relative to patients with isolated BKV viremia (FIG. 9) The threshold value of 10$^2$ was defined in the group of patients with BKV Nx as a function of the extent of the non-Gaussian distribution of the intensity of this response in order to consider up to the 90$^{th}$ percentile of normalized anti-BKV TCm values (FIG. 9).

In one preferred embodiment of the invention, only the proliferation of CD8$^+$ T cells is measured in step b), Without this being limiting, the inventors were able to show better discrimination of patients with BKV Nx based on CD8$^+$ T cells compared to CD4$^+$ T cells (FIG. 10). It is possible that this improved effect is due to the importance of the direct action mediated by CD8$^+$ T cells in the control of intra-parenchymal BKV replication (from an immunological viewpoint, while CD4$^+$ T cells contribute to the development and maintenance of an effective CD8$^+$ response, it is actually the CD8$^+$ T cells that will infiltrate the transplant and destroy the cells infected with BKV).

In this embodiment, the proportion of CFSE$^{low}$ CD8$^+$ T cells [measured in step b) and expressed for 10$^6$ total CD8$^+$ T cells] is thus normalized for 10$^3$ copies of BKV per mL of blood and then compared to the threshold of 10$^2$ in order to classify patients according to the level of risk for BKV Nx, as explained in the characterization of the index of the invention below.

The assessment of the proportion of $CFSE^{low}$ anti-BKV TCm as well as the measurement of the BKV viral load will preferably be repeated during the patient's life, due to the evolving nature of the values of these parameters after transplantation.

c) Step c: Measuring the Number of HLA Incompatibilities Between the Donor and the Recipient This step consists of measuring the number of HLA incompatibilities between the donor and the recipient of the kidney transplant.

Assessment of the Number of HLA Incompatibilities Between the Donor and the Recipient HLA (human leukocyte antigens) correspond to the major histocompatibility complex (MHC). It refers to specialized proteins (antigens) present on the surface of all cells (including leukocytes) and the genes that code for them. The MHC performs the function of presenting the antigen to allow recognition by the T cell through its antigen-specific receptor (TCR). The extreme diversity (genetic polymorphism) of the MHC is, in fact, a main determinant of the acceptance or rejection of organ transplantation between individuals.

HLA typing identifies the major HLA genes of the individual and the corresponding antigens that are present on the cell surface. This typing can be performed by serological or molecular techniques (by PCR).

For each transplant donor-recipient pair, an "HLA incompatibility number" is determined at the time of transplantation according to the standard methods described in the art.

This incompatibility number is the number of different donor HLA antigens (HLA-A, -B, -DR, -DQ) relative to the recipient. It must be done during the kidney transplantation because it largely guarantees the success of the transplantation. For the risk of transplant rejection to be minimal, it is important that the donor and recipient HLA antigens be as close as possible. This is why, in all of the kidney transplantations performed in 2016 from a deceased donor, more than 90% of recipients had fewer than 6 HLA incompatibilities with their donor [28].

The rules for calculating HLA compatibilities are well known. For example, if the donor is type HLA-A3 and -A33 and the recipient is type HLA-A33 and -A33, the donor/recipient pair have 1 incompatibility in HLA-A. If, in contrast, the donor is type HLA-A33 and -A33 and the recipient is type HLA-A3 and -A33, no HLA incompatibilities are counted. This calculation method for HLA incompatibilities has been thoroughly described in the scientific literature.

HLA incompatibilities are generally assessed at the time of kidney transplantation. This is a fixed assessment (i.e. not progressive).

The potential effect of HLA incompatibilities on BKV virus reactivation and the development of BKV Nx has been described in a few studies with conflicting results. This is probably explained by the heterogeneity of the definitions concerning the different BKV reactivations in the literature (distinction between viruria, viremia and BKV Nx). While HLA incompatibilities are associated with plasma BKV replication ([16], [18]), their impact on the development of BKV Nx remains poorly understood. One of these, Awadalla Y. et al. ([11]) showed in 2004 that these nephropathies are associated with a high level of HLA incompatibilities. These authors therefore suggested that a reduction in the number of HLA incompatibilities would reduce the risk of developing these nephropathies. An important comment concerning this study is that this association was documented in patients with BKV Nx compared to patients without BKV Nx, without specifying the presence of any viremia or viruria in patients without BKV Nx. Conversely, more recent studies report the occurrence of BKV Nx also in a context of good HLA compatibility between the donor and the recipient ([17]; [19]). Finally, other authors have found an inverse relationship in patients with BKV Nx between a low level of HLA incompatibility and a higher frequency of transplant loss ([15]).

Based on the results that permitted developing the present method, the inventors showed a lower number of HLA incompatibilities in patients with BKV-Nx. Patients with BKV Nx had a lower total number of HLA incompatibilities [HLA-A, -B, -DR, -DQ] relative to patients with isolated BKV viremia (FIG. 11a). Moreover, this number of HLA incompatibilities was negatively correlated to the BKV viral load (FIG. 11b).

From these results, the threshold value of 5 HLA incompatibilities in HLA-A, -B, -DR and -DQ was integrated as the genetic parameter in the calculation of the present method. This threshold value of 5 has been identified as a function of the extent of the non-Gaussian distribution of the number of HLA incompatibilities in order to take into account up to the $75^{th}$ percentile of HLA incompatibilities in the group of patients with BKV viremia (FIG. 11a).

Compilation of the Results for Calculating the Diagnostic Index of the Invention The three parameters a), b) and c) described above are then compiled to create a stratification index of the risk that the patient will develop a BKV Nx. Thus, the present inventors do not propose using the three parameters a), b) and c) in isolation, but rather combining them with one another in order to create the method of the invention and assess the risk of developing BKV Nx. FIG. 12 shows all the decision-making steps leading to assessing this BKV Nx risk according to the method of the invention Indeed, as described in the examples below and in FIGS. 12 and 13, there are threshold values defined from combinations of the three parameters of the invention that allow distinguishing patients with a high risk of developing BKV Nx from those who will not develop it.

Based on the cohort used in the examples of the present invention, these threshold are:

5 for the number of HLA incompatibilities and $10^2$ normalized intensity measurement units for the anti-BKV TCm response.

The present inventors have thus demonstrated that a normalized intensity of the anti-BKV TCm response less than or equal to (≤) $10^2$ associated with a total number of HLA incompatibilities less than or equal to (≤) 5 reflects a high risk that the patient receiving the transplant will one day develop a BKV Nx in the short, medium or long term (FIG. 13—dark gray dial).

Conversely, a normalized intensity of the anti-BKV TCm response strictly greater than (>) $10^2$ associated with a total number of HLA incompatibilities strictly greater than (>) 5 reflects a very low risk that the patient receiving the transplant will one day develop a BKV Nx in the short, medium or long term (FIG. 13—white dial).

In cross-sectional analysis of the cohort used in the examples of the present application, 100% of patients with a normalized intensity of the anti-BKV TCm response≤$10^2$ and a total number of HLA incompatibilities≤5 had BKV Nx (FIG. 13, dark gray dial). Conversely, no patient having a normalized intensity of the anti-BKV TCm response$>10^2$ and a total number of HLA incompatibilities$>5$ had BKV Nx (FIG. 13, white dial).

These thresholds (5 for the number of HLA incompatibilities and $10^2$ for the normalized intensity measurement units for the anti-BKV TCm response) have been established from the specific case of the cohort studied to develop the present invention. These thresholds could evolve and/or be refined depending on the results of a larger cohort followed longitudinally. The present inventors could more generally adapt the method of the invention in order to take into account the specific features of such a population. In particular, to obtain the index of the invention, it will be possible for the present inventors to study the values of the three parameters a), b) and c) mentioned above, to combine them and to identify the appropriate thresholds and adequate normalization values according to the results and graphical methods obtained from the analysis of such a population (graphical method in the format of FIGS. 12 and 13).

In the particular case of the cohort studied, three levels of risk were identified by the inventors on the basis of their analyses, performed on more than 27 renal transplant patients (including 11 patients with BKV viremia and 16 patients with BKV Nx):

A high level of risk for BKV Nx in the case of a normalized intensity of anti-BKV TCm response$\leq 10^2$ a positive predictive value of 100% (probability of BKV Nx if the test is positive) when the result of the method is a high level of risk for BKV Nx, a negative predictive value of 100% (probability of absence of BKV Nx if the test is negative) when the result of the method is a low level of risk for BKV Nx, a sensitivity of more than 60% (probability of a positive test in the case of BKV Nx) when the result of the method is an intermediate level of risk for BKV Nx, A zero false positive rate (a positive test being defined by a normalized intensity of anti-BKV TCm response$\leq 10^2$ and a total number of HLA incompatibilities$\leq 5$) in the case where the method indicates a high level of risk for BKV Nx.

Thus, the index of the invention has a positive predictive value greater than that conventionally described in the literature for the evaluation of the risk of BKV Nx as a function of the blood viral load of BKV (100% vs. 55%), as well as a zero false positive rate in the case where the method indicates a high level of risk for BKV Nx. Table 1 illustrated the performances of the different tests associated with predicting the risk of BKV Nx (as a function of the blood viral load of BKV vs. the method of the invention).

TABLE 1

Performances of the different tests associated with predicting the risk of BKV Nx (as a function of the blood viral load of BKV vs. the method of the invention).

| Study | Technique | Positivity threshold | PPV % | NPV % |
|---|---|---|---|---|
| Present inventors | Present invention: Combination of 3 biomarkers | Normalized intensity measurement unit of the anti-BKV TCm response $\leq 10^2$ and Number of HLA incompatibilities $\leq 5$ | 100 | 100 |
| Chung et al. [25] | Plasma BKV PCR | $>10^4$ copies/mL | 54.5 | 100 |
| Godinho Pinto et al. [26] (meta-analysis) | Plasma BKV PCR | $>4.2 \log_{10}$ | 50 | 100 |
| Godinho Pinto et al. [26] (meta-analysis) | Plasma BKV PCR | $\geq 3.7 \log_{10}$ | 29 | 100 | and a total number of HLA incompatibilities$\leq 5$ (FIG. 13—dark gray dial). This risk level is in favor of an increased risk of BKV Nx. Since strong immunosuppression is a risk factor for BKV Nx, this risk level argues for a substantial reduction in immunosuppression and close monitoring of the viral load and kidney function.

An intermediate level of risk for BKV Nx in the presence of a normalized intensity of anti-BKV response$\leq 10^2$ and a total number of HLA incompatibilities$>5$ (FIG. 13—light gray dial lower right) or in the presence of a normalized intensity of anti-BKV response$>10^2$ and a total number of HLA incompatibilities$\leq 5$ (FIG. 13—light gray dial upper left). This risk level should be considered an intermediate level of risk for BKV Nx.

A low level of risk for BKV Nx in the presence of a normalized intensity of anti-BKV TCm response$>10^2$ and a total number of HLA incompatibilities$>5$ (FIG. 13—white dial). This risk level is in favor of a low risk of BKV Nx. In this situation, surveillance of the viral load and kidney function should be recommended. Immunosuppression can be maintained or slightly reduced.

In the specific case of the cohort studied, this index has demonstrated the following excellent technical characteristics:

The method of the invention is therefore preferably characterized in that a high risk of developing BKvirus (BKV) nephropathy is diagnosed if:

a) in relation with a viral load of $10^3$ copies of BKV virus per mL of blood, b) the normalized intensity of the anti-BKV CD4$^+$ or CD8$^+$ TCm response is less than or equal to 100 intensity measurement units, and c) the number of incompatibilities between said patient and the donor of the transplanted kidney is less than or equal to 5.

The method of the invention is also preferably characterized in that a high risk of developing BKV virus (BKV) nephropathy is diagnosed if:

a) in relation with a viral load of $10^3$ copies of BKV virus per mL of blood, b) the normalized intensity of the anti-BKV CD4$^+$ or CD8$^+$ TCm is strictly greater than 100 intensity measurement units, and c) the number of HLA incompatibilities between said patient and the donor of the transplanted kidney is strictly greater than 5.

Diagnostic and Prognostic Use of the Index of the Invention.

Since it is not invasive, the method of the invention could be reproduced as often as necessary in patients at risk (typically, patients who have undergone kidney transplantation). Its frequency could be personalized according to each patient's profile, or in view of the results of the preceding tests. Moreover, it will be possible to adjust the dose of immunosuppressive treatments in a personalized manner, upward or downward, using the result of this index. Treatment reduction will be prescribed only for patients with BKV Nx or those whose risk of developing it is high. Patients for whom this reduction would not be beneficial or would even be harmful for the transplant (typically patients with isolated BKV viremia without involvement of the kidney transplant) will be identified and the treatment initially prescribed can be maintained.

> It is recommended to perform the method of the invention for each patient who had kidney transplantation and at regular time intervals. This recurrence could:
> Help diagnose BKV Nx
> Specify the risk level of developing BKV Nx individually in order to prevent the occurrence of such a complication.
> Assess the patient's therapeutic immunosuppression, and, in particular, guide immunosuppressive treatment adjustment in order to prevent any deficiency or excess of therapeutic immunosuppression.

In a preferred embodiment, the method of the invention is performed at the same time as the dosage of immunosuppressive treatments to be administered to said patient. A test concluding a high risk of BKV Nx would be in favor of a reduction of immunosuppressive treatment in order to prevent its occurrence.

In an even more preferred embodiment, the method of the invention is repeated several times during the post-transplantation treatment, for example every 3 to 6 months in the population of patients at risk of developing BKV Nx (patients with viremia and/or having undergone transplant rejection treatment and/or having unexplained deterioration of kidney transplant function).

In addition to routine performance in al patients presenting BKV viremia, it is recommended to conduct the method of the invention in the following situations:

During treatment intensification in the context of curative treatment for transplant rejection, in order to assess the subsequent risk of BKV Nx occurrence.

During reduction of immunosuppression after a first positive test, in order to assess the impact of this reduction on the anti-BKV TCm response.

In the event of unexplained deterioration of the kidney transplant function in order to assess the risk and/or aid the diagnosis of BKV Nx.

The method of the invention could be performed 2 to 3 months after modification of the immunosuppressive treatment. The result of the method of the invention could help define the time for increasing immunosuppressive treatment again in a patient, if an immune response develops.

FIG. 14 shows the different indications for the method of the invention as well as the time period for repeating said method.

Thus, FIG. 15 illustrates the approach proposed to assess the risk of BKV Nx. This novel approach is initially based on longitudinal monitoring of the BKV viral load in the patient's blood from the threshold of positivity of the BKV viral load ($\geq$200 copies/mL of blood). Unlike the usual approach for BKV Nx (FIG. 3), this novel approach is not conditioned by performing a kidney transplant biopsy, but rather by the use of the method of the invention. The application of the present method permits stratifying the level of risk for BKV Nx in kidney transplant patients with blood BKV reactivation. Without this being limiting, only patients with a risk of BKV NX assessed as intermediate to high will actually have a minimization of immunosuppressive treatment. Patients with a low risk of BKV Nx will not have a minimization of immunosuppressive treatment. In all cases, a regular monitoring of the BKV viral load and the repetition of said method will also be recommended. The present invention permits assessing the risk of BKV Nx before kidney transplant dysfunction. It saves time and permits effective stratification of BKV Nx risk, ultimately helping to guide therapeutic immunosuppression (FIG. 15).

The present application also relates to an in vitro method for assessing the response of a kidney transplant patient to blood replication of BKV after modification of immunosuppressive treatment, characterized in that the method defined above (index of the invention) is repeated at regular time intervals after transplantation.

Preferably, the method of the invention is repeated before and after each treatment modification.

Preferably, the method of the invention is repeated every 3 to 6 months approximately, at a frequency depending on the level of plasm BKV reactivation and/or the need to modify the immunosuppressive treatment of said patient.

Immunosuppressive treatments currently used in kidney transplantation are, for example:

At the initial time of kidney transplantation, induction treatments combining high-dose corticosteroids and polyclonal anti-lymphocytic antibodies (anti-human thymocyte immunoglobulins, Thymoglobulin® or Grafalon®) or anti-CD25 monoclonal antibodies (Basiliximab, Simulect®);

As a followup to induction treatments, maintenance treatments combining
    a low-dose corticotherapy,
    a calcineurin inhibitor (tacrolimus, Prograf® or cyclosporine, Neoral®) and a purine base synthesis inhibitor (mycophenolate mofetil, CellCept®),
    or even molecules such as mTOR pathway inhibitors (everolimus, Certican®) or CTLA4-Ig (belatacept, Nulojix®) [1].

If the method of the invention detects a significant risk of developing BKV Nx, the therapeutic management should lead to reduction of immunosuppression, or possibly to a change in treatment.

KEY TO FIGURES

FIG. 1 describes the frequency of BKV reactivation after kidney transplantation in terms of BKV viruria, isolated BKV viremia, BKV Nx and chronic dysfunction/loss of kidney transplants [4,5,6,7].

FIG. 2 describes the outcome at 3 years from the kidney transplant in patients with or without BKV Nx (a—kidney function assessed by measuring the glomerular filtration rate (GFR) in ml/min/1.73 $m^2$, Kruskal-Wallis test and b—kidney transplant survival, Kaplan-Meier and log-rank test).

i) a virological parameter assessed by the BKV viral load in the patient's blood,
    ii) an immunological parameter assessed by the intensity of the anti-BKV TCm response in the patient, and iii) a genetic parameter assessed by the number of HLA incompatibilities in the [donor/recipient] pair.

FIG. 5 shows the BKV viral load levels in the blood (a) and urine (b) of different patient groups of the cohort studied here (nonparametric Kruskal-Wallis test). The threshold used in the method of the invention ($10^3$ copies/mL of BKV in the blood) was defined from these results in order to allow risk to be assessed as early as possible.

Figure 3:
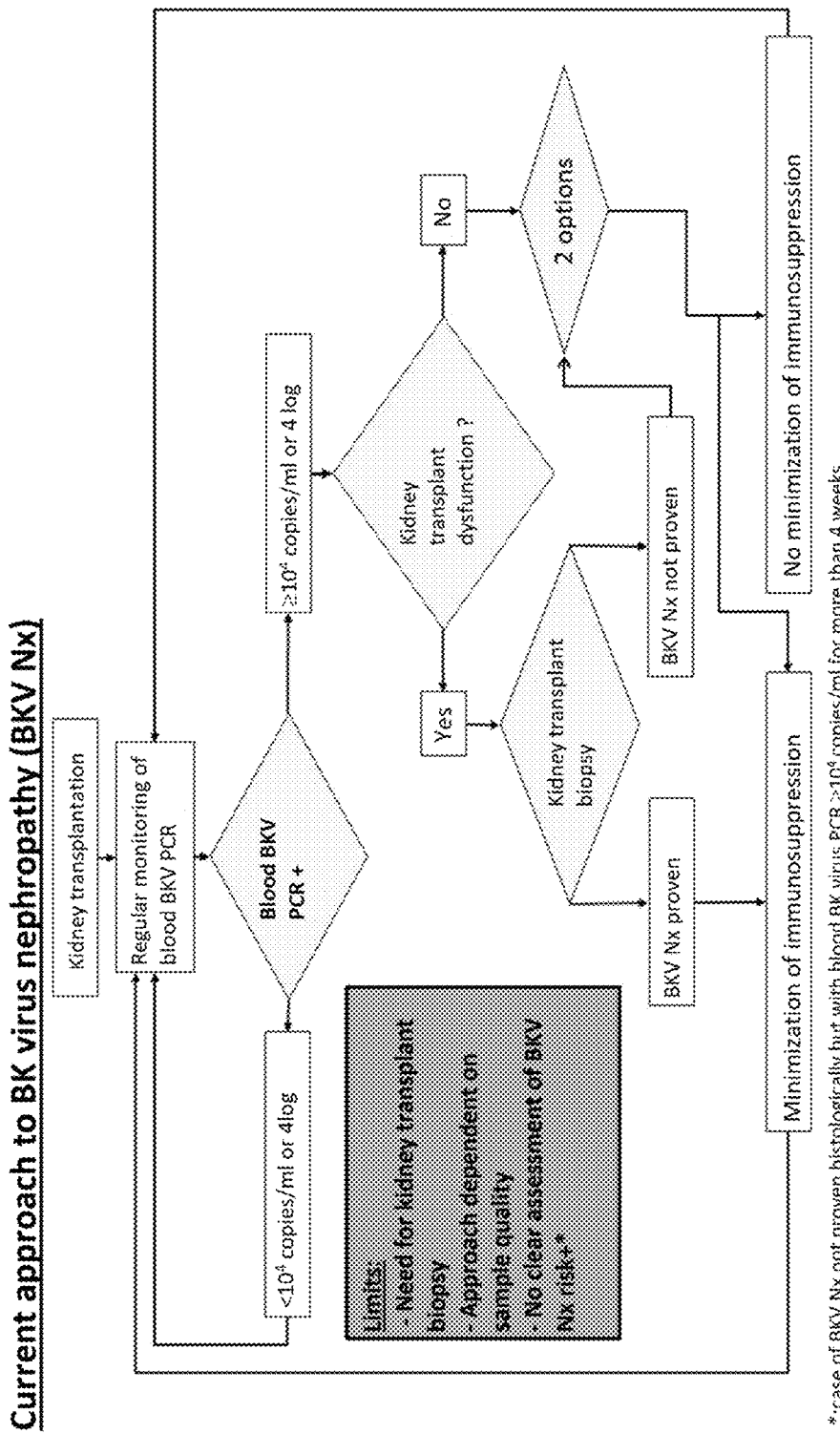
FIG. 3 shows the current approach for BKV Nx, based on assessment of the blood BKV viral load and kidney transplant biopsy.
Figure 4:
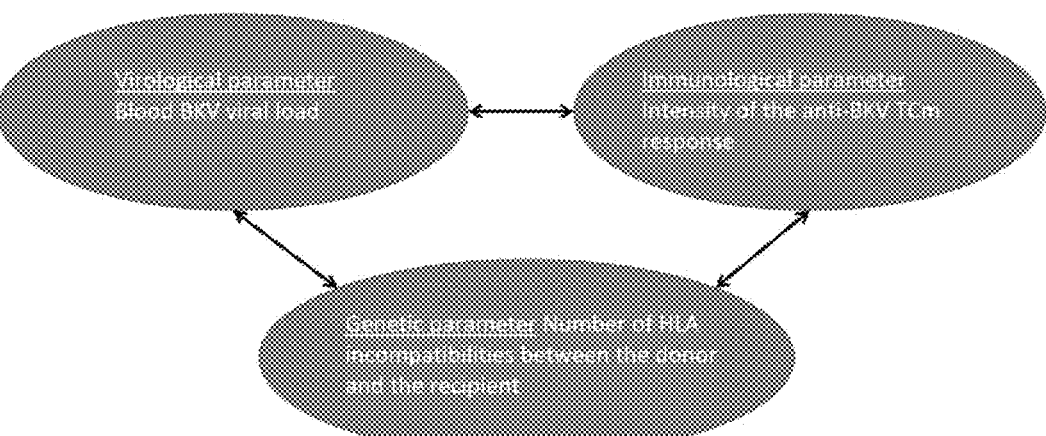
FIG. 4 shows the method of the invention based on the combination of three parameters.
Figure 6:
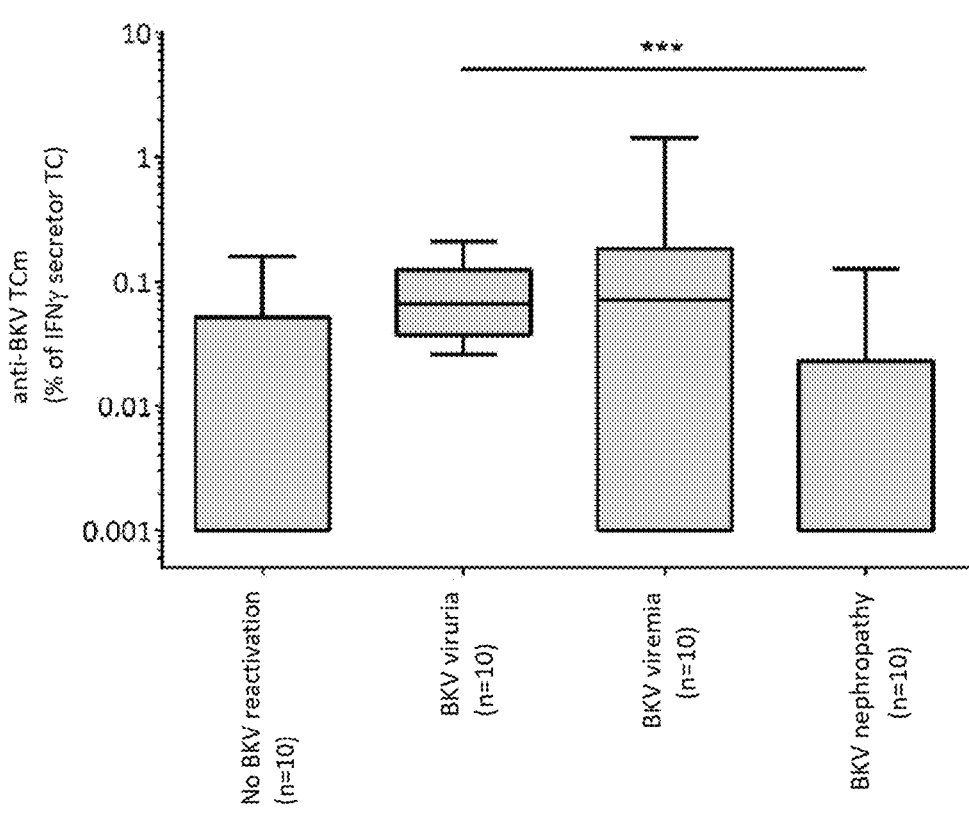
Figure 6:
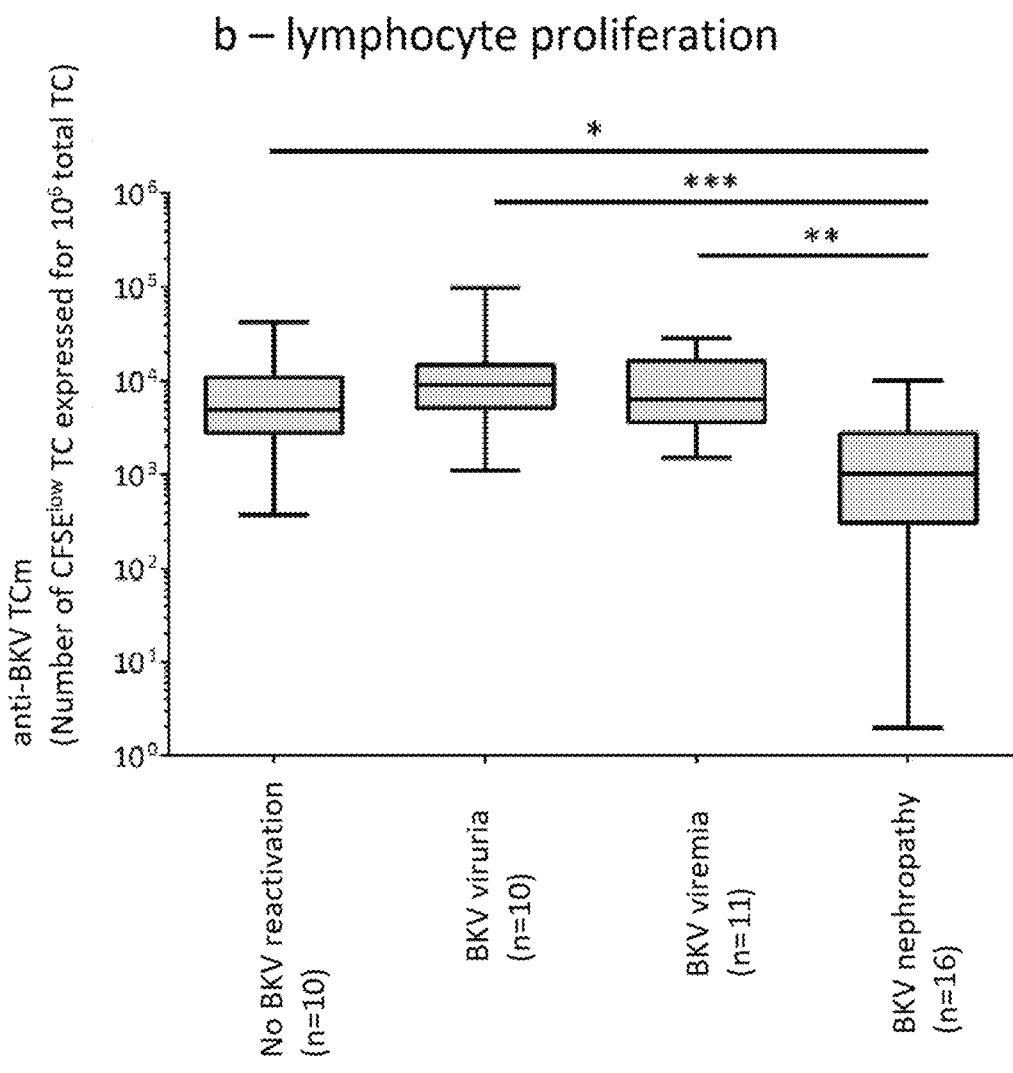
Figure 6:
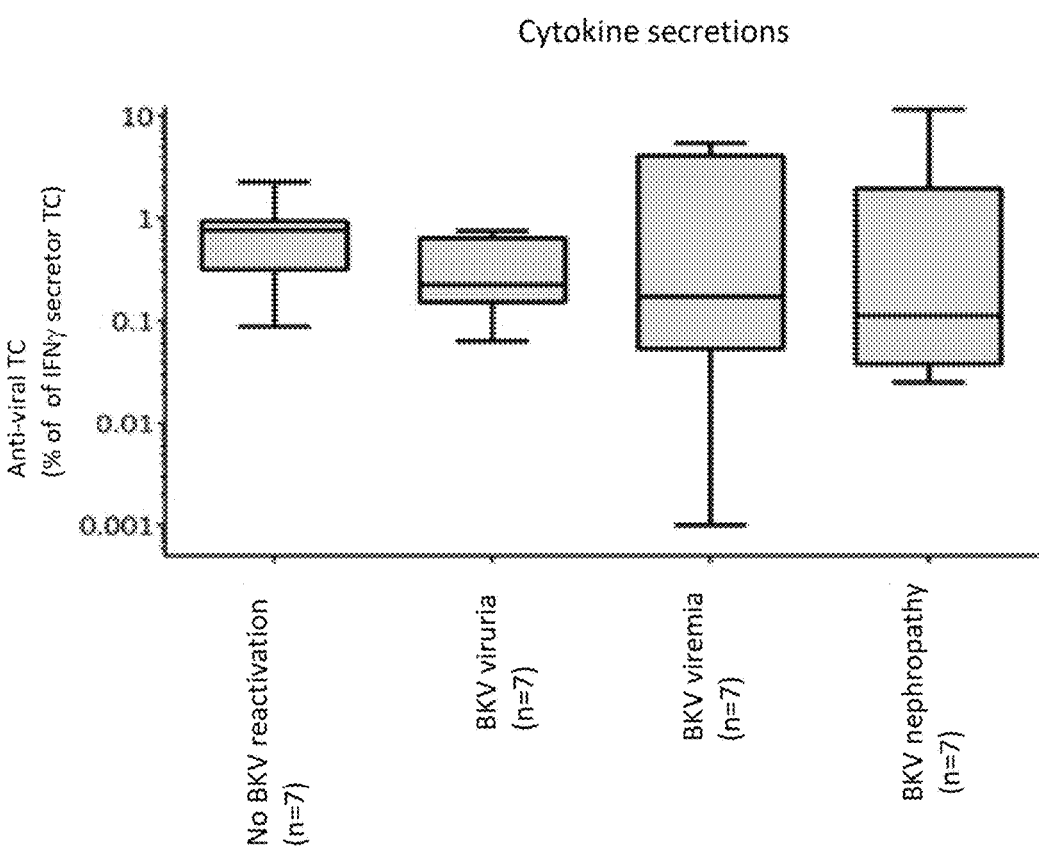
Figure 6:
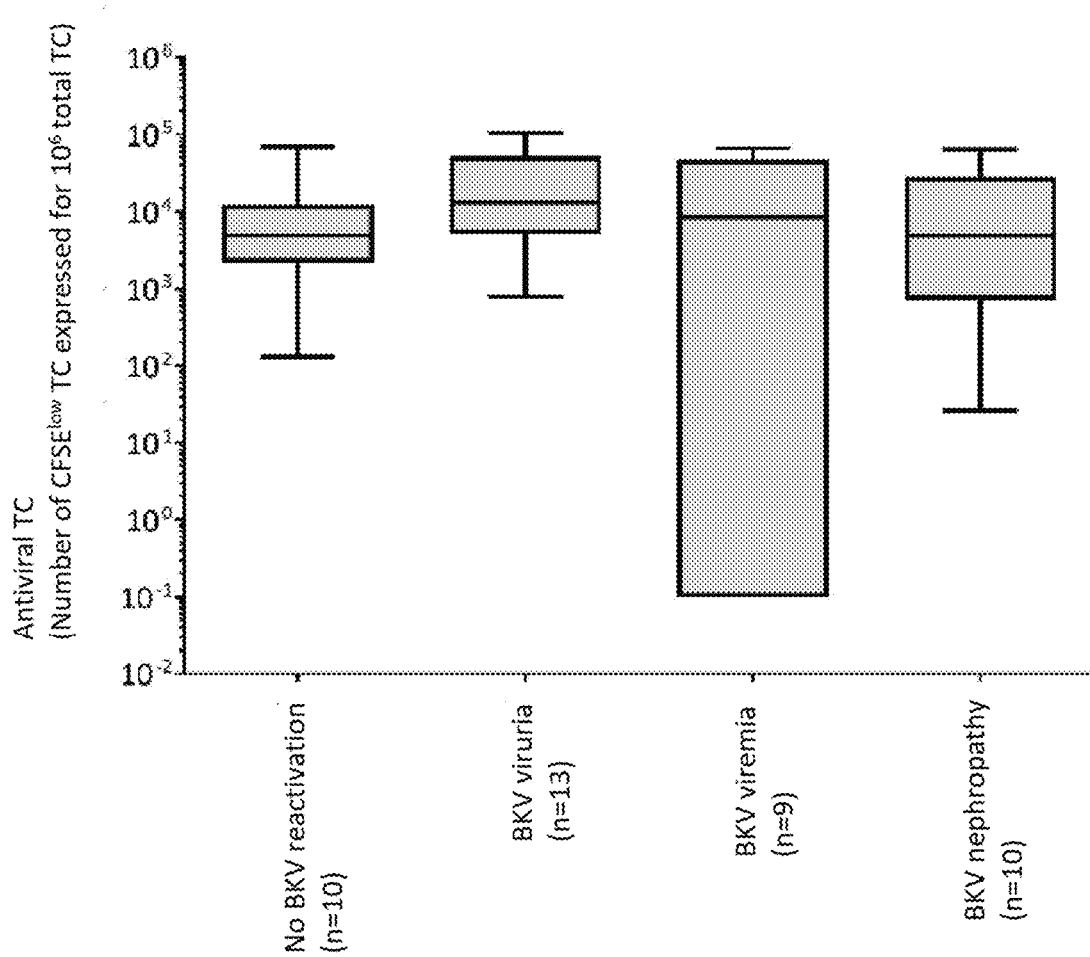

FIG. 6—part 1 shows the different lymphocyte functionality tests conducted after stimulation with specific BKV peptides. Cytokine secretion (1*a*) and lymphocyte proliferation (1*b*) were used to assess the anti-BKV TCm response in the different groups of patients of the cohort studied here (TC: T cells; nonparametric Kruskal-Wallis test).

FIG. 6—part 2 shows the different lymphocyte functionality tests conducted after stimulation by a mix of antiviral peptides (peptides covering cytomegalovirus, Epstein-Barr and influenza virus). Cytokine secretion (2*a*) and lymphocyte proliferation (2*b*) were used to assess the overall memory T cell antiviral response in the different groups of patients of the cohort studied here (no significant differences).

Figure 7:
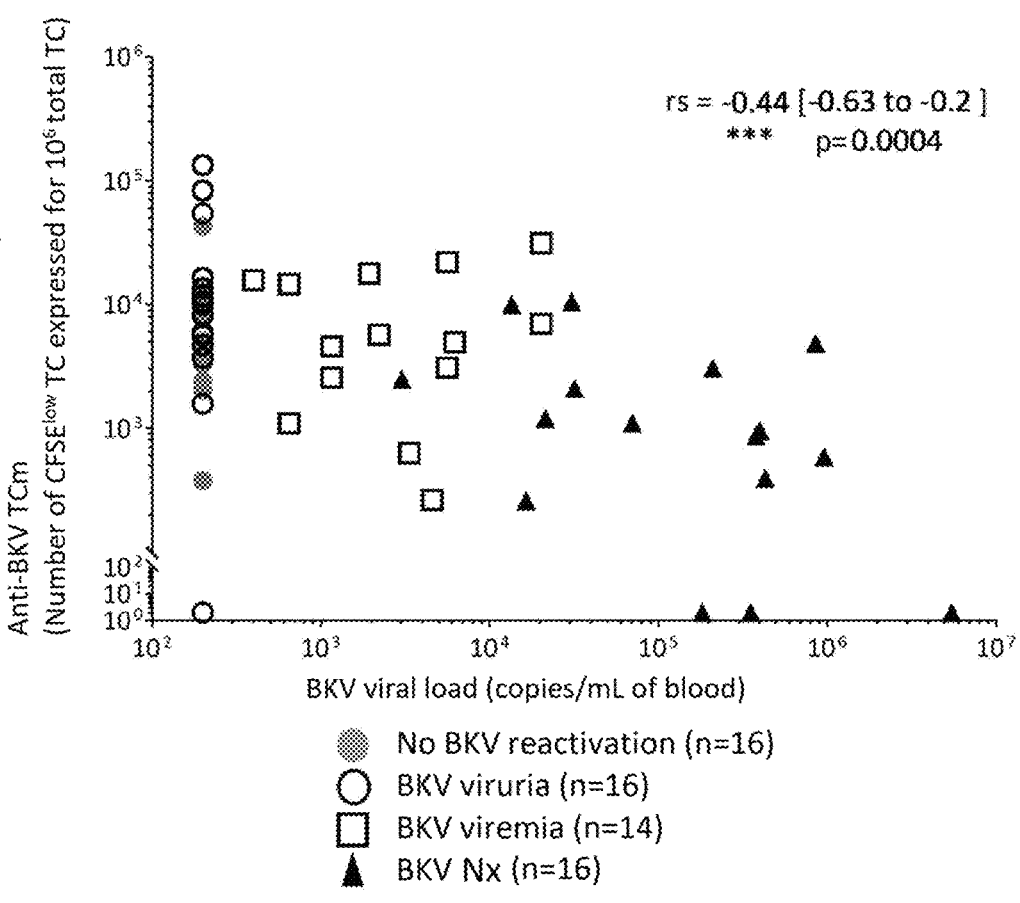

FIG. 7 shows the negative correlation between the intensity of the anti-BKV TCm response and the BKV viral load (copies/mL of blood) (nonparametric Spearman's correlation test).

FIG. 8/1 illustrates the assessment protocol for the anti-BKV TCm response, via the analysis of the proliferation of anti-BKV TCm in response to a pool of specific BKV peptides (proportion of CFSE$^{low}$ T cells). The proportion of anti-BKV TCm having actively proliferated (proportion of CFSE$^{low}$ TC) is measured by subtracting the proportion of CFSE$^{low}$ TC measured in the absence of peptide stimulation from the proportion of CFSE$^{low}$ TC measured in the presence of specific BKV peptides.

FIG. 8/2 shows the assessment of the normalized intensity of anti-BKV TCm response. The normalized intensity of anti-BKV TCm response is quantified in "normalized intensity measurement units". A "normalized intensity measurement unit" is defined here as being the proportion of CFSE$^{low}$ anti-BKV TCm expressed for $10^6$ total T cells and normalized for $10^3$ copies of BKV per mL of blood. This normalization allows an intra and inter-individual comparison [here, inter-individual comparison (isolated BKV viremia vs. BKV Nx)].

Figure 9:
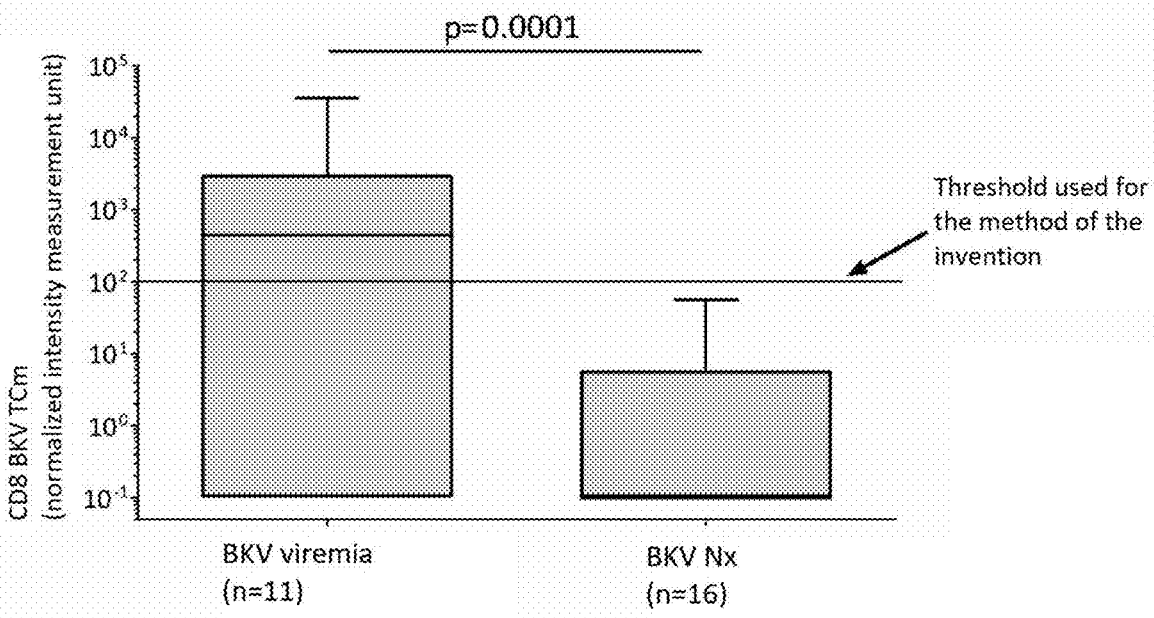

FIG. 9 shows the normalized intensity of the anti-BKV CD8$^+$ TCm cell response in patients with isolated BKV viremia (n=11) or BKV Nx (n=16). The only threshold used in the method of the invention ($10^2$ normalized measurement intensity units) was defined from the results in order to take into consideration up to the $90^{th}$ percentile of the response intensity values demonstrated in patients with BKV Nx.

Figure 10:
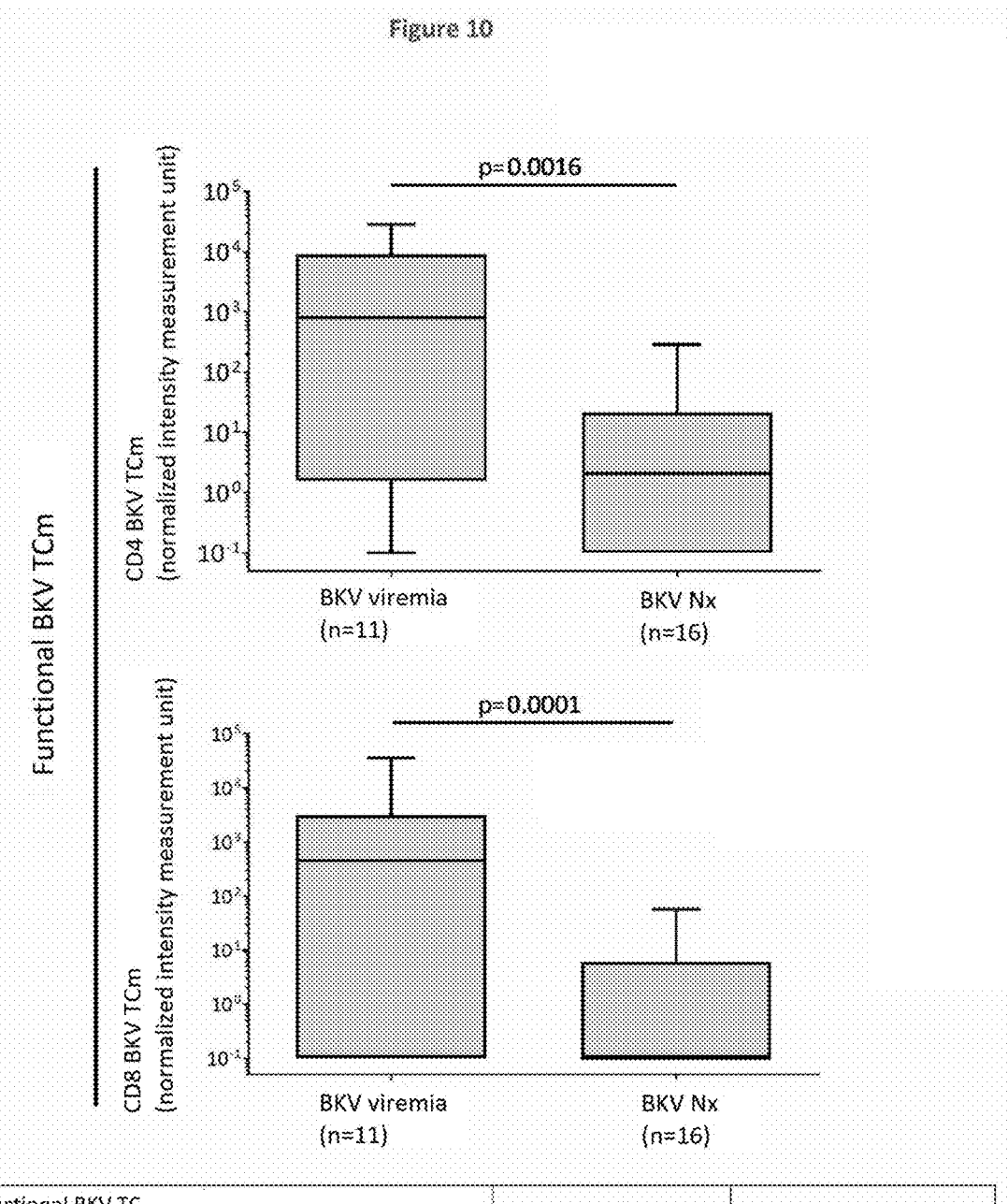

FIG. 10 shows the comparison of the normalized intensity of the anti-BKV TCm response in type CD4 and CD8 lymphocytes in patients with isolated BKV viremia (n=11) and patients with BKV Nx (n=16).

FIG. 11*a* shows a lower number of HLA incompatibilities [HLA-A, -B, -DR, -DQ] between the transplant donor and recipient in patients with BKV Nx compared to patients with isolated BKV viremia (Mann-Whitney test). The threshold used in the method of the invention (5 HLA incompatibilities [HLA-A, -B, -DR, -DQ] between the transplant donor and recipient) was defined from these results in order to take into consideration up to the $75^{th}$ percentile of the HLA incompatibility values in patients with isolated BKV viremia.

FIG. 11*b* shows the negative correlation between the number of HLA incompatibilities and BKV viremia (in number of copies/mL of blood) (nonparametric Spearman's correlation test).

Figure 12:
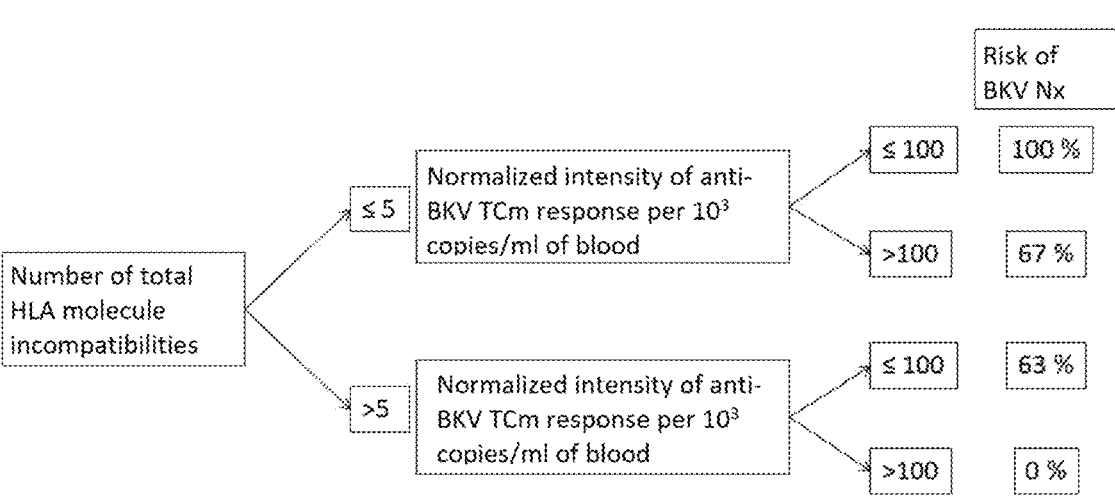

FIG. 12 is a stratification tree for the BKV Nx risk according to the 3 parameters defined above.

Figure 13:
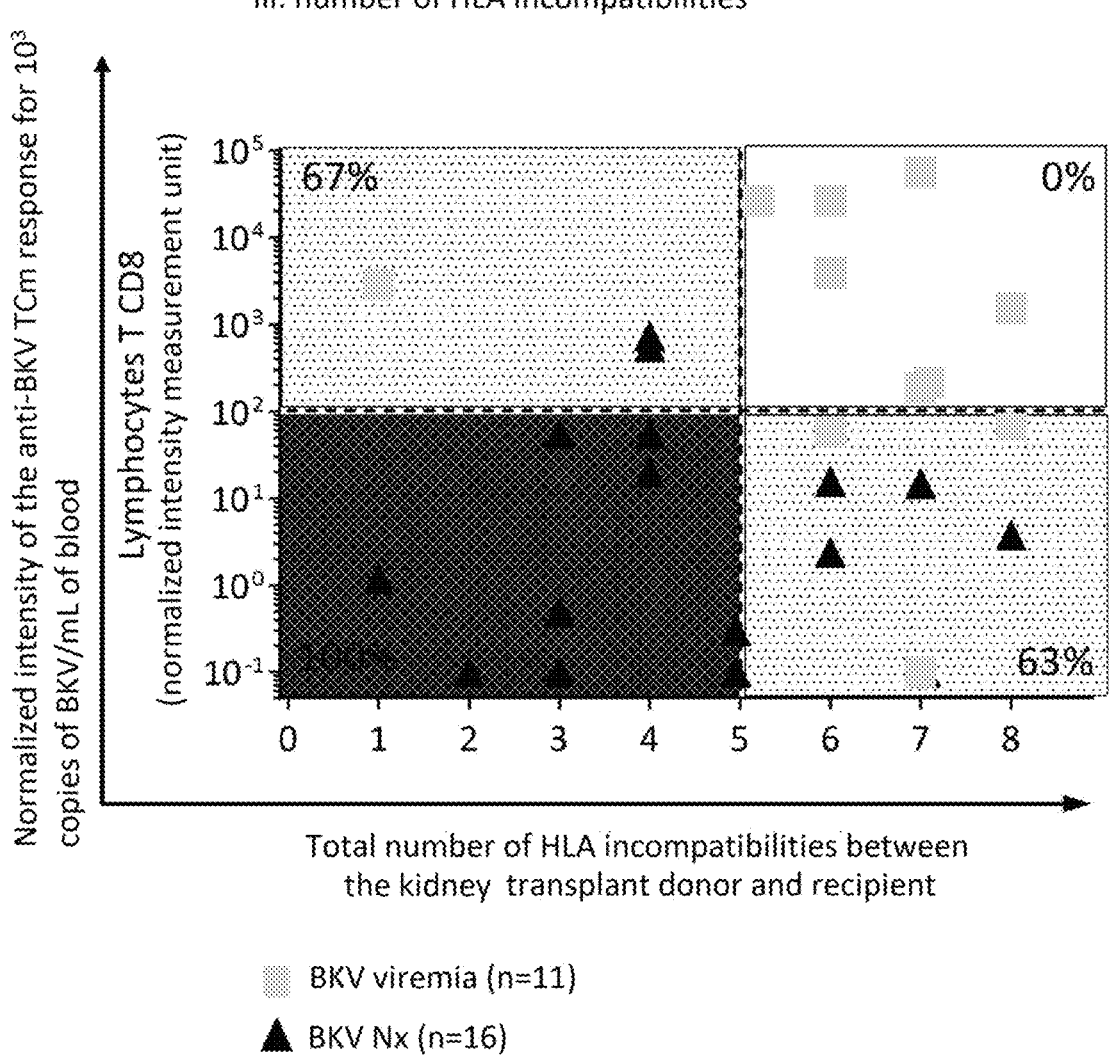

FIG. 13 describes the level of risk of developing BKV Nx after kidney transplantation in cases of BKV viremia as a function of the following three parameters:
  i. the intensity of the anti-BKV TCm response normalized to,
  ii. the BKV blood viral load ($10^3$ copies of BKV per mL of blood), and
  iii. the number of HLA incompatibilities between the donor and the recipient.

Figure 14:
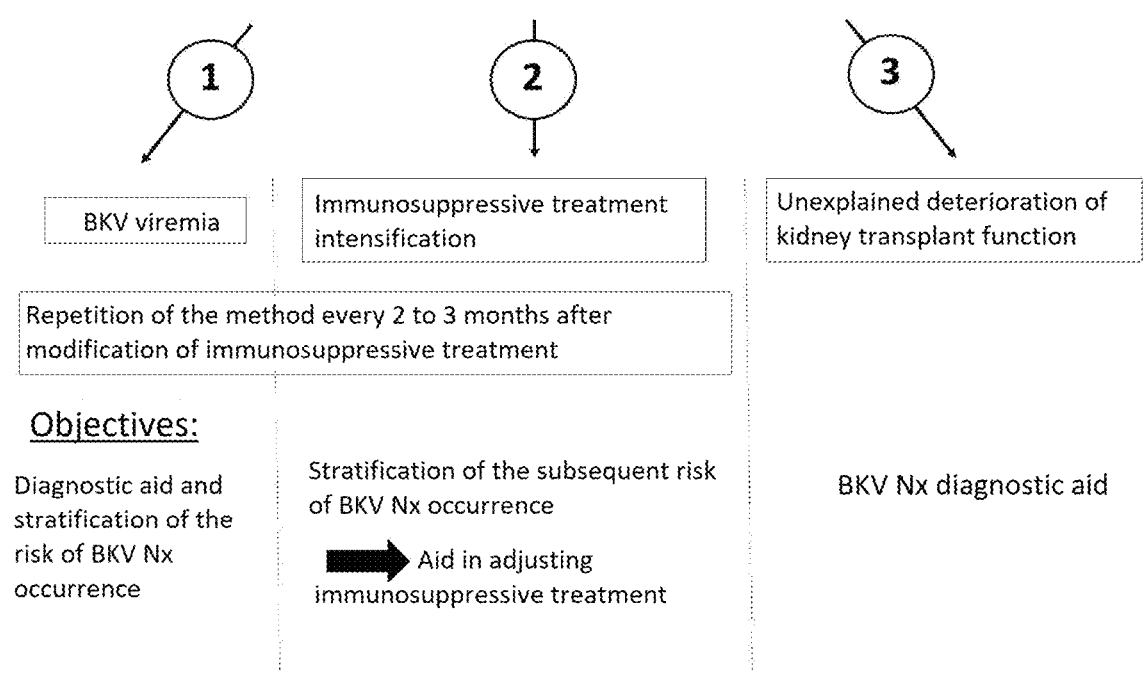

FIG. 14 shows the different indications for the method of the invention as well as the time interval for repeating said method.

Figure 15:
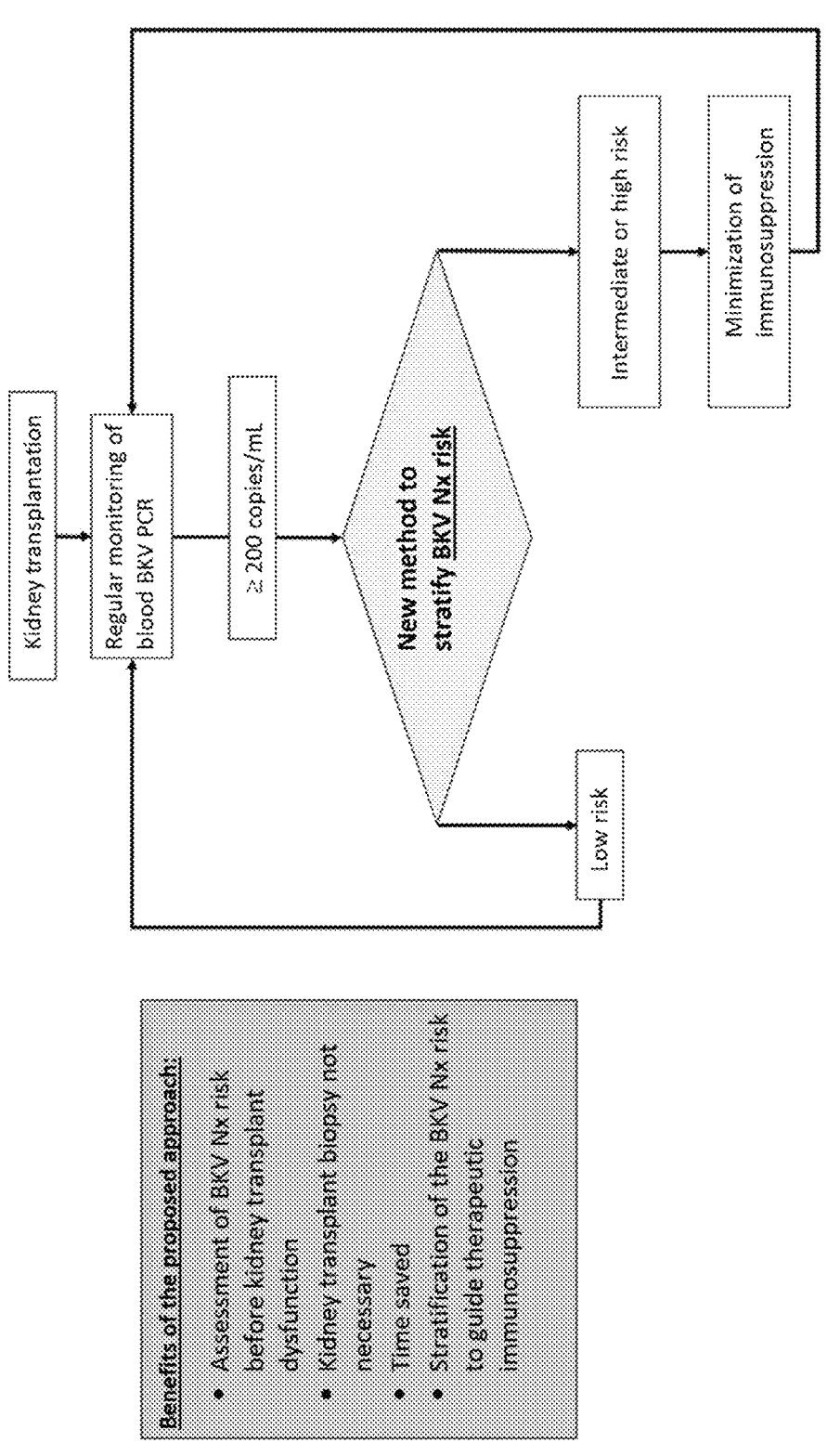

FIG. 15 shows the approach proposed here for assessing BKV Nx risk, based on assessment of the blood BKV viral load and the method of the invention.

EXAMPLES

Materials and Methods:

In order to characterize the specific cellular response for BKV post-kidney transplantation, the present inventors conducted an observational study including 94 kidney transplant patients. The patients enrolled were all from the Nephrology Department of Bicêtre Hospital (University Hospitals of South Paris). In all, this site performs more than 130 kidney transplants per year with an active file of more than 2000 patients monitored with a functional kidney transplant. The CPP Ile de France [ethics committee] was consulted and did not find any ethical obstacle to conducting this study. An information letter was given to all the patients and their consent was collected in writing.

This study started in November 2014 with a duration of enrollment of 36 months (enrollment finished on Nov. 1, 2017). The inclusion criteria were the following:
  ➢ patents above age 18,
  ➢ no other organ transplantation except for the kidney one,
  ➢ no active chronic HIV/HBV/HCV infection.

Four groups of BKV virus reactivation were defined in these kidney transplant patients according to the criteria below:
  ➢ patients without BKV reactivation:
    plasma and urine BKV viral loads undetectable for at least 12 months.
  ➢ patients with BKV viruria:
    positive BKV viruria (>200 copies/ml) and
    BKV viremia undetectable for at least 12 months
  ➢ patients with isolated BKV viremia:
    positive BKV viremia (>200 copies/ml) for at last 6 months and
    no histological diagnosis of BKV Nx on kidney transplant biopsy
  ➢ patients with BKV Nx:
    diagnosis of BKV Nx on kidney transplant biopsy with positive BKV viremia (>200 copies/ml)

In order to characterize the anti-BKV TCm in the different groups of patients in this cohort, the present study included a clinical aspect (exhaustive collection of clinical and biological data over a prospective followup of 36 months) as well as an immunological aspect (study of peripheral blood mononuclear cells (PBMC) in a peripheral blood sample).

Regarding the clinical part of the study, the following clinical and biological data were collected as art of a longitudinal followup of 36 months:

➤ Age, sex, initial kidney disease, method and length of dialysis for the recipient ➤ Characteristics of the kidney transplantation:
Age of the kidney transplantation
Donor type
Transplantation rank (first transplant or second/third/ etc. transplant).

➤ Organ transplant rejection

➤ Reactivation of BKV virus:
Blood and urine BKV viral loads (expressed in copies/ mL)
Duration of replication (expressed in months)

➤ Estimate of the glomerular filtration rate according to the MDRD formula:
At 1 month and 6 months post transplant
At diagnosis of BKV Nx or at 12 months post transplant
At the end of followup ➤ Immunosuppressive treatment
Induction treatment and maintenance treatment
Residual amount of immunosuppressants
at diagnosis of BKV Nx or at 12 months post kidney transplantation
Immunosuppressive treatment changes following the diagnosis of BKV Nx.

Table 2 shows the absence of difference in terms of therapeutic immunosuppression (nature and intensity of immunosuppressive treatment) in the different groups of kidney transplant patients (NS=not significant).

PBMC were isolated on average. This documents the relative lymphopenia of the patients (between 0.5 and 0.6 million PBMC/mL of blood).

The anti-BKV TCm response was characterized in the different patient groups. A specific activation of anti-BKV TCm was done by culturing PBMC with an overlapping peptide pool covering the BKV VP1 and LT-Ag proteins (PepTivator BKV, Miltenyi® or equivalent). These peptide pools activate CD4 and CD8 T cells and cover the two cycles of BKV replication (LT-Ag for the early phase and VP1 for the late phase of BKV virus replication). After activation by specific BKV peptides, the lymphocyte polyfunctionality of anti-BKV TCm was evaluated by flow cytometry in terms of:

➤ Cytokine secretions:
overnight incubation of 4 million PBMC (800,000 PBMC/condition) in the presence of specific BKV proteins and brefeldin A (cytokine secretion inhibitor) then
study of the IL2, IFN-$\gamma$ and TNF-$\alpha$. synthesis capacities.

➤ Lymphocyte proliferation:
culture of 4 million PBMC labeled with CFSE (500, 000 PBMC/condition) for 5 days in the presence of specific BKV peptides then
study of the proliferation capacities by visualization of the CFSE dilution.

All the flow cytometry acquisitions were done in an 18-color cytometer (BD LSRFortessa™ or equivalent) and the analyses were done in FlowJo specific analysis software. Statistical Methodology Used:

TABLE 2

| Immunosuppressive treatment in the different groups of kidney transplant patients (NS = not significant). | | | | |
|---|---|---|---|---|
| Immunosuppressive treatment | Without BKV reactivation | BKV viruria | BKV viremia | BKV NX | P |
| n | 25 | 25 | 22 | 22 | |
| INDUCTION TREATMENT (n, %) | 23 (92) | 22 (88) | 22 (100) | 21 (95.5) | NS |
| Polyclonal depleting antibodies (n, %) | 11 (47.8) | 6 (27.3) | 11 (50) | 12 (57.1) | NS |
| Anti-CD25 monoclonal antibodies (n, %) | 12 (52.2) | 16 (72.7) | 11 (50) | 9 (42.9) | |
| MAINTENANCE TREATMENT before diagnosis of BKV nephropathy | | | | | |
| Tacrolimus (n, %) | 18 (72) | 19 (76) | 15 (68.2) | 17 (77.3) | NS |
| Residual amount of tacrolimus (ng/ml, median with interquartile) | 9.1 [8.1-11.4] | 9.1 [8.4-10.4] | 9.1 [7.7-11.1] | 8.6 [6.6-10.1] | NS |
| Antimetabolites (n, %) | 23 (92) | 23 (92) | 15 (68.2 | 18 (81.8) | NS |
| Glucocorticoids (n, %) | 25 (100) | 25 (100) | 22 (100) | 22 (100) | NS |
| TRANSPLANT REJECTION TREATMENT before diagnosis of BKV nephropathy | | | | | |
| Intravenous glucocorticoid bolus (n, %) | 5 (20) | 5 (20) | 8 (36.4) | 10 (45.5) | NS |
| Polyclonal depleting antibodies (n, %) | 1 (4) | 1 (4) | 3 (13.6) | 1 (4.6) | NS |
| Plasma exchanges (n, %) | 1 (4) | 4 (16) | 5 (22.7) | 4 (18.2) | NS |
| RITUXIMAB (n, %) | 2 (8) | 2 (8) | 4 (18.2) | 2 (9.1) | NS |

Concerning the immunological part of the study, a single blood draw of 15 mL of whole blood (3 lithium heparin tubes of 5 mL) was performed at baseline. This blood draw was done during the histological assessments performed for the usual patient followup. In the groups with isolated BKV viremia and BKV Nx, a longitudinal followup was also conducted, with a new sample taken at 12 and 24 months from baseline in order to assess the progress of the anti-BKV TCm response. From 15 mL of whole blood, 8 to 10 million Continuous variables are expressed in median with interquartile range [25-75] given the absence of normal distribution of the data and the small number of subjects (n<30). These variables were compared by using Mann-Whitney or Kruskal-Wallis nonparametric tests according to the comparison of two or more distributions. The correlations were tested by using the nonparametric Spearman's correlation test.

The categorical variables are expressed in percentages. The chi-squared test was used to compare the proportions between the different groups. The survival functions were done according to the Kaplan-Meier estimator, with the log-rank comparison test.

The statistical significance threshold was established for a p-value<0.05 The statistical analysis was performed with GraphPad Prism software.

Development of the Method of the Invention:

a) Measurement of the Proliferation of Memory T Cells Specific for BKV

This lymphocyte functionality test based on the assessment of the anti-BKV TCm proliferation capacities after activation by BKV peptides was specifically developed by the present inventors.

FIG. 8/1 illustrates the protocol for identification of anti-BKV TCm that proliferated, in response to a specific stimulation by BKV virus peptides, from whole blood of kidney transplant patients.

PBMC comprising anti-BKV TCm were obtained from a 15-mL blood sample of whole blood for each patient. This blood sample is of the peripheral venous type, taken with 3 lithium heparin tubes (tubes with green caps) of 5 mL (FIG. 8/1a).

The proliferation test for anti-BKV TCm requires around 5 to 6 million PBMC; the blood sample provides 8 to 10 million.

The PBMC were isolated by FICOLL gradient C (PAN Biotech®—reference P04-60505 or equivalent). From 15 mL of whole blood, the present inventors isolate 8 to 10 million PBMC on average (FIG. 8/1b).

The PBMC were cultured for 5 days with two pools of BKV peptides at the final concentration of 1 μg/mL/peptide. The peptide pools are sold by Miltenyi Biotec (PepTivator® BKV VP1—reference: 130-097-272 and PepTivator® BKV LT—reference: 130-096-504) or equivalent (FIG. 8/1c). The LT-Ag and VP1 peptide sequences used are immuno-dominant peptides widely recognized in the scientific literature as able to activate anti-BKV TCm. The stronger of the two responses was considered for the identification of functional anti-BKV TCm.

The T cell proliferation was measured by addition, on the day of culture, of a lymphocyte proliferation marker (Cell-Trace CFSE Thermo Fisher Scientific®—reference: C34554). Other equivalent lymphocyte proliferation markers could also be used. On the fifth day of cell culture, the PBMC were labeled by the following antibodies [BD® anti-CD3 antibodies (reference: 564712), Miltenyi® CD4 (reference: 130-096-900) and Miltenyi® CD8 (reference: 130-096-561) or equivalent] and analyzed by flow cytometry (BD LSRFortessa™ cytometer or equivalent) (FIG. 8/1d). CD4 and CD8 TCm specific for BKV are identified and counted on the basis of the degree of CFSE labeling (CFSE$^{low}$ T cells). As explained above, the proportion of anti-BKV TCm having actively proliferated (proportion of CFSE$^{low}$ TC) is measured by subtracting the proportion of CFSE$^{low}$ TC measured in the absence of peptide stimulation from the proportion of CFSE$^{low}$ TC measured in the presence of specific BKV peptides (FIGS. 8/1e and 8/2a).

The proportion of functional anti-BKV TCm is then expressed for $10^6$ total T cells and then normalized for $10^3$ copies of BKV per mL of blood. FIG. 8/2 illustrates this normalization of the proportion of functional anti-BKV TCm in order to permit an assessment of the normalized intensity of the anti-BKV TCm response. The assessment of the intensity of this response permits an intra- and inter-individual comparison.

b) Measurement of Viral Load

The BKV viral load was measured via a specific commercial kit (BKV R-GENE®—reference 69-013B from BioMérieux® or equivalent). The biological sample used can be a whole blood or plasma sample from said patient.

c) Measurement of the Number of HLA Incompatibilities Between the Donor and the Recipient All HLA typings in the context of transplantation are done by the St Louis HLA laboratory (which centralizes these tests on Ile de France. The HLA typing of the recipient is currently done by next-generation allelic sequencing techniques (allelic sequencing of HLA A, B, C, DRB1, DQB1, DQA1 and DPB1 molecules—MiSeq device from Illumina® or equivalent). HLA donor typing is done on an emergency basis, at the time of the kidney transplantation by a "Sequence Specific Primers method" (Linkage Biosciences, Thermo Fisher®) using SABR (Single Antigen Bead Resolution) kits or equivalent.

It is important to remember that donor and recipient HLA typing is routinely done according to the international recommendations for all kidney transplant patients at the time of the transplant in order to decide whether to proceed with the kidney transplantation. The results are transmitted to the medical teams via the Agence de la Biomédecine [French Biomedicine Agency].

Results:

Ninety-four kidney transplant patients were enrolled and divided into 4 groups according to their level of BKV virus reactivation:

➤ Patients without BKV reactivation (n=25):
   plasma and urine BKV viral loads<200 copies/mL
➤ Patients with BKV viruria (n=25):
   median urinary BKV viral load of $1.9 \times 10^4$ [$3.9 \times 10^3$–$1.8 \times 10^3$] copies/mL
   plasma BKV viral load (>200 copies/ml)
   median time until reactivation of 21.8 [14.6-34.7] months.
➤ Patients with isolated BKV (n=22):
   median plasma BKV viral load of $4.2 \times 10^3$ [$1.1 \times 10^3$–$1.2 \times 10^4$] copies/mL
   urinary BKV viral load of $1.1 \times 10^8$ [$6.2 \times 10^6$-$3.8 \times 10^8$] copies/mL
   median time until reactivation of 10.3 [5.6-21.1] months and 13.8 [9.3-27.1] months
   no histological diagnosis of BKV Nx on kidney transplant biopsy
➤ Patients with BKV Nx (n=22):
   histological diagnosis of BKV Nx on kidney transplant biopsy
   plasma BKV viral load of $2.8 \times 10^5$ [$3 \times 10^4$–$6.3 \times 10^5$] copies/mL
   urinary BKV viral load of $1 \times 10^9$ [$5.4 \times 10^7$-$1.8 \times 10^9$] copies/mL
   respective median time until reactivation of 12.6 [5.2-24.7] months and 13.8 [4-23.3] months FIG. 5 shows the different levels of blood and urinary BKV viral loads in the different patient groups as a function of the degree of BKV reactivation. In agreement with the prior art, it is important to note that while a plasma BKV viral load>$10^5$ can be associated with BKV Nx (FIG. 5a), this parameter is late because it is already associated with renal parenchymal damage and severe chronic dysfunction of the transplant at the time of diagnosis of BKV Nx (FIG. 2a). Furthermore, given the absence of difference between the urinary BKV viral loads in patients with isolated BKV viremia and BKV Nx, this parameter was not considered in the development of the invention.

Based on the clinical and biological data obtained to date, the average time to transplant for the entire cohort studied was 3.5 years. The median time to onset of BKV Nx was 12 months after kidney transplantation.

Due to standardized single-center management of immunosuppression, the groups were comparable in terms of immunosuppression (nature and intensity of immunosuppressive treatment—see Table 2).

A chronic severe kidney transplant dysfunction was found from the diagnosis of BKV Nx (p<0.0001, FIG. 2a). The renal outcome was also unfavorable with a higher rate of transplant loss in patients with BKV Nx compared to patients without BKV Nx (p<0.0001, FIG. 2b).

An impaired functionality of anti-BKV TCm was documented in patients with BKV Nx post-kidney transplantation. The group of patients with BKV Nx exhibited a lower anti-BKV TCm response:

in terms of cytokine secretion capacity: reduced interferon γ secretion capacity in the BKV Nx group relative to the group with BKV viruria (FIG. 6/1a).

in terms of lymphocyte proliferation capacity: reduced lymphocyte proliferation capacity in the BKV Nx group relative to the other three groups (patients without BKV reactivation, with BKV viruria and isolated BKV viremia (FIG. 6/1b).

This impairment of lymphocyte response was specific to anti-BKV TCm. Patients with BKV Nx possessed preservation of anti-viral responses after stimulation by a pool of peptides covering cytomegalovirus, Epstein-Barr and influenza viruses (CEF peptide pool from Axxora®, reference PT-PA-CEF-002 or equivalent—FIG. 6/2a-b).

The intensity of the anti-BKV TCm proliferative response was negatively correlated with the BKV viral load in the blood (FIG. 7). After normalization of the response intensity to $10^3$ copies of BKV/mL of blood, this normalized intensity of the anti-BKV response was significantly lower in patients with BKV Nx relative to patients with isolated BKV viremia (FIG. 9). These data suggest an alteration of the lymphocyte polyfunctionality of the anti-BKV TCm, suggesting a state of exhaustion of these lymphocytes.

Lymphocyte proliferation is the most discriminating assessment method for lymphocyte functionality. Moreover, this test allows specifically assessing central memory T cells and memory stem cells. However, as explained previously, the size of these lymphocyte subpopulations within the memory T cells specific to a pathogen determines their capacities for self-renewal, proliferation, help signals and differentiation into effectors. The specific assessment of these central memory and memory stem cells permits a more precise assessment of the immunological capacities for protection against BKV virus. The assessment of the cytokine secretion capacity makes it possible to preferentially study "terminal" memory cell subpopulations of the memory effector or terminal effector T cell type. These highly differentiated lymphocyte subpopulations have little, if any, self-renewal, proliferation or differentiation capacity ([13], [14]). This assessment method was therefore favored.

Moreover, as mentioned above, a smaller number of HLA incompatibilities has been documented in patients with BKV Nx. Patients with BKV Nx had a lower total number of HLA incompatibilities [HLA-A, -B, -DR, and -DQ] relative to patients with isolated BKV viremia (FIG. 11a). Moreover, this number of incompatibilities was negatively correlated to the BKV viral load (FIG. 11b).

From the data obtained, a stratification index of the risk of developing BKV Nx was developed.

In patients with BKV Nx, it was possible to document an association between:

a reduction in the normalized intensity of anti-BKV TCm response (intensity of response normalized for $10^3$ copies/mL of blood of BKV virus) and a low number of HLA molecule incompatibilities between the donor and the recipient.

Thus, in cross-sectional analysis of the cohort, 100% of patients with a normalized intensity of the anti-BKV TCm response≤$10^2$ and a total number of HLA incompatibilities≤5 had BKV Nx (FIG. 13, dark gray dial). Conversely, no patient having a normalized intensity of the anti-BKV TCm response>$10^2$ and a total number of HLA incompatibilities>5 had BKV Nx (FIG. 13, white dial).

REFERENCES

[1] Kidney Disease: Improving Global Outcomes (KDIGO) Transplant Work Group. KDIGO clinical practice guideline for the care of kidney transplant recipients. Am J Transplant. 2009; 9:S1-155.

[2] Agence de la Biomédecine. Rapport Annuel REIN (Réseau Epidémiologie et Information en Néphrologie) 2015. Disponible sur: https://www.agence-biomedecine.fr

[3] Maillart E, Taoufik Y, Gasnault J, Stankoff B. Leucoencéphalopathie multifocale progressive. EMC Neurol. 2017.

[4] Dalianis T, Hirsch H H. Human polyomaviruses in disease and cancer. Virology. 2013; 437:63-72.

[5] Hirsch H, Vincenti F, Friman S, Tuncer M, Citterio F, Wiecek A, et al. Polyomavirus BK replication in de novo kidney transplant patients receiving tacrolimus or cyclosporine: a prospective, randomized, multicenter study. Am J Transplant. 2013; 13:136-45.

[6] Hirsch H, Knowles W, Dickenmann M, Passweg J, Klimkait T, Mihatsch M J, et al. Prospective study of polyomavirus type BK replication and nephropathy in renal-transplant recipients. N Engl J Med. 2002; 347:488-96.

[7] Hirsch H, Babel N, Comoli P, Friman V, Ginevri F, Jardine A, et al. European perspective on human polyomavirus infection, replication and disease in solid organ transplantation. Clin Microbiol Infect. 2014; 20:74-88.

[8] Dekeyser M, Frangois H, Beaudreuil S, Durrbach A. Polyomavirus-Specific Cellular Immunity: From BK-Virus-Specific Cellular Immunity to BK-Virus-Associated Nephropathy? Front Immunol. 2015; 6:307.

[9] Sharma R., Tzetzo S., Patel S., Zachariah Mareena, Sharma S., Melendy T. BK virus in Kidney Transplant: current Concepts, Recent Advances and Future Directions, Experimental and Clinical Transplantation (2016): 4:377-384

[10] Limaye A P, Jerome K R, Kuhr C S, Ferrenberg J, Huang M L, Davis C L, Corey L, Marsh C L. Quantitation of BK virus load in serum for the diagnosis of BK virus associated nephropathy in renal transplant recipients. J. Infect. Dis. 2001

[11] Awadalla Y., Randhawa P., Ruppert K., Zeevi A., Duquesnoy R J. HLA Mismatching Increases the Risk of BK Virus Nephropathy in Renal Transplant Recipients. Am. J. Transplant 2004

[12] Sester M, Leboeuf C, Schmidt T & Hirsch H. The 'ABC' of Virus-Specific T Cell Immunity in Solid Organ Transplantation. Am. J. Transplant. (2016):16:1697-1706.

[13] Restifo, Nicholas P., et Luca Gattinoni. «Lineage Relationship of Effector and Memory T Cells». Current Opinion in Immunology (2013) 25 (5):556-63.

[14] Egli, A., Humar, A. & Kumar, D. State-of-the-art monitoring of cytomegalovirus-specific cell-mediated immunity after organ transplant: a primer for the clinician. Clin. Infect. Dis. (2012) 55, 1678-1689.

[15] Drachenberg, Cinthia B., John C. Papadimitriou, Dean Mann, Hans H. Hirsch, Ravinder Wali, et Emilio Ramos. 2005. «Negative Impact of Human Leukocyte Antigen Matching in the Outcome of Polyomavirus Nephropathy». Transplantation 80 (2): 276-78.

[16] Hissig, A., M. Roos, A. Etter, W. Bossart, N. Müller, M. Schiesser, R. P. Withrich, et T. Fehr. 2014. «Association of BK Viremia with Human Leukocyte Antigen Mismatches and Acute Rejection, but Not with Type of Calcineurin Inhibitor». Transplant Infectious Disease 16 (1): 44-54.

[17] Helanterä, Ilkka, Kaija Salmela, Lauri Kyllönen, Anne Räisänen-Sokolowski, Eeva Auvinen, Laura Mannonen, Petri Koskinen, et Irmeli Lautenschlager. 2012. «BK Virus Viremia in a Well-HLA-Matched Kidney Transplant Population Mainly on Low-Dose Cyclosporine-Based Immunosuppression». Clinical Transplantation 26 (6): E596-601.

[18] Thangaraju, Sobhana, Jagbir Gill, Allissa Wright, Jianghu Dong, Caren Rose, et John Gill. 2016. «Risk Factors for BK Polyoma Virus Treatment and Association of Treatment With Kidney Transplant Failure: Insights From a Paired Kidney Analysis». Transplantation 100 (4): 854-61.

[19] Ramos E, Drachenberg C B, Papadimitriou J C, et al. Clinical course of polyoma virus nephropathy in 67 renal transplant patients. J Am Soc Nephrol 2002; 13: 2145.

[20] Batal I. et al, Measurements of Global Cell-Mediated Immunity in Renal Transplant Recipients With BK virus reactivation. Am. J. Clin. Pathol. 2008; 129:857-591

[21] Comoli P. et al, Polyomavirus-associated nephropathy: update on BK virus-specific immunity. Transpl. Infect. Dis. 2006:8:86-94

[22] Schachtner T. et al, BY virus-Specific Immunity Kinetics: A predictor of Recovery From polyomavirus BK-associated nephropathy. Am. Journal. Of Transplantation, 2011; 11:2443-2452

[23] Schachtner T. et al, The Loss of BKV-specific immunity from Pretransplantation to Posttransplantation identifies Kidney Transplant Recipients at Increased Risk of BKV Replication. Am. Journal. Of Transplantation, 2015; 15:2159-2169

[24] Johnston, O. et al. Treatment of polyomavirus infection in kidney transplant recipients: a systematic review. Transplantation 89, 1057-1070 (2010).

[25] Chung, B. H. et al. Clinical usefulness of BK virus plasma quantitative PCR to prevent BK virus associated nephropathy. Transpl. Int. 25, 687-695 (2012).

[26] Godinho Pinto, G., Poloni, J., Rotta, L., R. Razonable, R. & Pasqualotto, A. Screening for BK virus nephropathy in kidney transplant recipients: comparison of diagnostic tests. J. Bras. Nefrol. 38, (2016)

[27] Comoli, P. et al. Immunity to Polyomavirus BK Infection: Immune Monitoring to Regulate the Balance between Risk of BKV Nephropathy and Induction of Alloimmunity. Clin. Dev. Immunol. 2013, 256923 (2013).

[28] Agence de la Biomédecine. Le rapport medical et scientifique du prélèvement et de la greffe en France en 2016. (2016).

---

The invention claimed is:

1. A method for assessing the risk of developing a BK virus (BKV) nephropathy in a patient who had kidney transplantation from a kidney donor, said method comprising the following steps:

a) measuring the viral load of BKV in a biological sample of said patient, b) measuring the normalized intensity of the CD4$^+$ or CD8$^+$ memory T cell response specific for BKV in a biological sample from said patient, said normalization being performed relative to the BKV viral load measured in step a), and c) determining the number of HLA allele differences between the kidney donor and said patient, wherein a high risk of developing BKV nephropathy is concluded when:

in relation with a viral load of $10^3$ copies of BK virus per mL of blood, the normalized intensity of the CD4$^+$ or CD8$^+$ memory T cell response specific for BKV is less than or equal to 100 intensity measurement units, and the number of differences between said patient and the donor of the transplanted kidney is less than or equal to 5.

2. The method according to claim 1, wherein the three parameters a), b) and c) are then compiled to create a stratification index for the risk that the patient will develop BK virus nephropathy.

3. The method according to claim 1, wherein the BKV viral load is measured in step a) by quantitative PCR from a sample of whole blood or plasma from said patient.

4. The method according to claim 1, wherein the response of the BKV specific CD4$^+$ or CD8$^+$ memory T cells measured in step b) is determined by contacting peripheral blood mononuclear cells from said patient with BKV peptides, and by assessing the proliferation of T cells present in said mononuclear cells after 4 to 7 days of culture.

5. The method according to claim 1, wherein the response of the BKV specific CD4$^+$ or CD8$^+$ memory T cells measured in step b) is determined by contacting peripheral blood mononuclear cells from said patient with BKV peptides, and by assessing the proliferation of T cells present in said mononuclear cells after 4 to 7 days of culture by determining the proportion of CD4$^+$ T cells having diluted a proliferation marker after 4 to 7 days of culture in the presence of said peptides.

6. The method according to claim 1, wherein the response of the BKV specific CD4$^+$ or CD8$^+$ memory T cells measured in step b) is determined by contacting peripheral blood mononuclear cells from said patient with BKV peptides, and by assessing the proliferation of T cells present in said mononuclear cells after 4 to 7 days of culture by determining the proportion of CD8$^+$ T cells having diluted a proliferation marker after 4 to 7 days of culture in the presence of said peptides.

7. The method according to claim 1, wherein a low risk of developing BK virus (BKV) nephropathy is concluded when:

a) in relation with a viral load of $10^3$ copies of BK virus per mL of blood, b) the normalized intensity of the CD4$^+$ or CD8$^+$ memory T cell response specific for BKV is greater than 100 intensity measurement units, and c) the number of differences between said patient and the transplant donor is greater than 5.

8. An in vitro method for assessing the response of a kidney transplant patient to blood replication of BKV comprising providing said patient immunosuppressive treatment, modifying said patient's immunosuppressive treatment, and then performing the method of claim 1 repeatedly at regular time intervals after said kidney transplant.

9. The method according to claim 1, wherein said method is an in vitro method for assessing the response of a kidney transplant patient to blood replication of BKV after modification of immunosuppressive treatment, and wherein said method is repeated before and after each treatment modification.

10. The method according to claim 1, wherein said method is an in vitro method for assessing the response of a kidney transplant patient to blood replication of BKV after modification of immunosuppressive treatment, and wherein said method is repeated approximately every 3 to 6 months.

11. A kit containing:

a) reagents for conducting BK virus quantitative PCR, and b) reagents for conducting the immunological method described in claim 4 on whole blood.

12. The kit according to claim 11, wherein the reagents b) contain BKV peptide sequences or polyclonal lymphocyte stimulation peptide sequences and, optionally, lymphocyte labeling reagents.

13. The kit according to claim 11 containing:

a) specific primers for amplifying portions of the BKV genome, and b) BKV peptide sequences, and, optionally c) the reagents necessary for conducting quantitative PCR with DNA extraction and/or d) the reagents for lymphocyte labeling.

* * * * *